(12) United States Patent
Korc et al.

(10) Patent No.: US 7,108,986 B2
(45) Date of Patent: Sep. 19, 2006

(54) GLYPICAN-1 IN HUMAN BREAST CANCER

(75) Inventors: Murray Korc, Irvine, CA (US);
Arthur D. Lander, Laguna Beach, CA (US)

(73) Assignee: The Regents of the University of California, Oakland, CA (US)

( * ) Notice: Subject to any disclaimer, the term of this patent is extended or adjusted under 35 U.S.C. 154(b) by 649 days.

(21) Appl. No.: 10/210,327

(22) Filed: Jul. 31, 2002

(65) Prior Publication Data

US 2003/0103980 A1    Jun. 5, 2003

Related U.S. Application Data

(63) Continuation-in-part of application No. 09/807,575, filed as application No. PCT/US99/24176 on Oct. 15, 1999.

(60) Provisional application No. 60/309,722, filed on Jul. 31, 2001, provisional application No. 60/121,624, filed on Feb. 25, 1999, provisional application No. 60/104,510, filed on Oct. 16, 1998.

(51) Int. Cl.
*C12Q 1/00*     (2006.01)
*G01N 33/53*    (2006.01)
*G01N 33/567*   (2006.01)
*G01N 33/574*   (2006.01)
*G01N 33/48*    (2006.01)

(52) U.S. Cl. ............ 435/7.1; 435/4; 435/7.2; 435/7.21; 435/7.23; 436/63; 436/64; 436/86; 436/164; 436/174; 436/512; 436/536; 424/130.1; 424/138.1; 530/300; 530/350; 530/385; 530/386; 530/387.1; 530/387.3; 530/387.7; 530/387.9; 530/388.1; 530/391

(58) Field of Classification Search ............ 435/4, 435/7.1, 7.2, 7.21, 7.23; 436/63, 64, 86, 436/164, 512, 536, 87, 174; 530/300, 350, 530/385, 386, 387.1, 387.3, 387.7, 387.9, 530/388.1, 391; 424/130.1, 138.1
See application file for complete search history.

(56) References Cited

OTHER PUBLICATIONS

Matsuda et al. Glypican-1 is overexpressed in human breast cancer and modulates the mitogenic effects of multiple heparin-binding growth factors in breast cancer cells. Cancer Research 61(14): 5562-5569, Jul. 15, 2001.*

Kleeff et al. The cell-surface heparin sulfate proteoglycan glypican-1 regulates growth factor action in pancreatic carinoma cells and is overexpressed in human pancreatic. J. Clin. Invest. 102(9): 1662-1673, Nov. 1, 1998.*

* cited by examiner

*Primary Examiner*—Alana M. Harris
(74) *Attorney, Agent, or Firm*—Rutan & Tucker, LLP

(57) ABSTRACT

Glycosylphosphatidylinositol-(GPI-) anchored HSPG glypican-1 is strongly expressed in human breast and pancreatic cancer—both by the cancer cells and in the case of pancreatic cancer the adjacent fibroblasts—whereas expression of glypican-1 is low in the normal pancreas and in chronic pancreatitis. Treatment of two pancreatic cancer cell lines, which express glypican-1, with the enzyme phosphoinositide-specific phospholipase-C (PI-PLC) abrogated their mitogenic responses to two heparin-binding growth factors: fibroblast growth factor-2 (FGF2) and heparin-binding EGF-like growth factor (HB-EGF). Treatment of MDA-MB-231 and MDA-MB-468 breast cancer cells with PI-PLC abrogates the mitogenic response to two heparin-binding growth factors, heparin-binding epidermal growth factor-like growth factor (HB-EGF) and fibroblast growth factor-2 (FGF-2). Syndecan-1 is also expressed at high levels in breast cancer tissues as well as breast cancer cells by comparison with breast normal tissues. Temporary or permanent transfection of a glypican-1 antisense construct attenuated glypican-1 protein levels and the mitogenic response to FGF2 and HB-EGF. Glypican can be used to detect the carcinoma in vitro and therapeutics that either bind to (e.g., antibodies or drugs), remove (e.g., enzymes) or prevent the expression (e.g., antisense constructs) of surface of the extracellular domain of glypican-1 are effective in retarding the growth of glypican-responsive carcinomas.

4 Claims, 30 Drawing Sheets

A

Wild-type
Sham
PG#7
PG#18
PG#19

◂ endogenous glypican-1

◂ glyp1-VSVGTMR

B

◂ c-myc epitope

A. glypican-1

B. glypican-3

C. glypican-4

D. syndecan-1

7S

MDA-MB-231    MDA-MB-468 non-reducing  reducing    non-reducing  reducing

A. mRNA
7S

B. total lysate

C. secreted component

GLYPICAN-1 IN HUMAN BREAST CANCER

The present application is a continuation-in-part of application Ser. No. 09/807,575, filed on Jul. 12, 2001, which is the National Phase filing of PCT/US99/24176, filed on Oct. 15, 1999, which claims priority from U.S. Provisional Application No. 60/104,510 (filed Oct. 16, 1998) and Ser No. 60/121,624 (filed Feb. 25, 1999). The present application is also a continuation-in-part of and claims priority from U.S. Provisional Application No. 60/309,722 (filed Jul. 31, 2001). All of the above applications are incorporated herein by reference.

BACKGROUND OF THE INVENTION

1. Field of the Invention

The present application concerns medical sciences and more particularly detection and treatment of human cancers, especially breast cancer.

2. Description of Related Art

Membrane associated heparan sulfate proteoglycans (HSPGs) are thought to play important roles in many aspects of cell behavior, including cell-cell and cell-extracellular matrix adhesion (59, 104) and growth factor signaling (13, 89). Two families of polypeptides appear to carry the majority of the heparan sulfate on mammalian cells: glypicans, which are attached to the plasma membrane via glycosylphophatidylinositol (GPI) anchors, and syndecans, which are transmembrane proteins (13, 7). Four syndecans and five glypicans, all encoded by separate genes, have been described to date (6, 14, 107, 23, 117 and 97). Many of these polypeptides exhibit tissue specific patterns of expression, although these patterns often overlap (38, 64, 2 and 9). In vitro, at least, it is common for cells to express multiple HSPGs, often from both the glypican and syndecan families.

The binding of heparin-binding growth factors to their cell surface receptors often requires the presence of cell-surface heparan sulfate proteoglycans (HSPGs) (27, 37, 90). There are two families of molecules, syndecans and glypicans, that differ significantly in core protein domain structure (13, 7). Five members of the glypican family (glypican-1-5) and four members of the syndecan family (syndecan-1-4) have been reported to date (64, 4). They have important functions with respect to cell behavior, including cell-cell and cell-extracellular matrix adhesion (59, 104), growth factor signaling (13, 89) and protection of growth factors such as FGF-2 from thermal denaturation and proteolytic attack (96, 102). They also regulate the interaction of several heparin-binding growth factors with their respective receptors and, consequently, their biological activity (99).

The role of HSPGs in growth factor signaling has been best characterized with respect to fibroblast growth factors (FGFs), which require the presence of heparan sulfate for high affinity binding to their tyrosine kinase receptors (88, 120, and 8). More recently, several other growth factors have been found to exhibit a strong requirement for an HSPG coreceptor in their signaling; these include heparin-binding EGF-like growth factor (HB-EGF), hepatocyte growth factor (HGF), and members of the Wnt family of secreted glycoproteins (27, 94, 37, and 90). Many other growth factors, including vascular endothelial growth factor (VEGF), platelet derived growth factor (PDGF), transforming growth factor-βs (TGF-βs), and bone morphogenetic proteins (BMPs), are known to bind heparin and heparan sulfate, although the physiological consequences of this binding are unclear.

Pancreatic cancer is responsible for over 20% of deaths due to gastrointestinal malignancies, making it the fourth to fifth most common cause of cancer related mortality. The prognosis of patients with pancreatic cancer is extremely poor, with 5-year survival rates lower than 5% (116). The reasons for this biological aggressiveness have not been clearly elucidated. Nonetheless, previous work has established that these cancers overexpress many mitogenic growth factors and their receptors (44) including a number of heparin-binding growth factors such as FGF1, FGF2, FGF5, HB-EGF, and amphiregulin. (119, 20, 4, and 48).

The mortality of breast cancer in the United States has recently leveled off and even decreased slightly (1, 2). However, breast cancer remains the second most common cause of cancer death in women in the United States (51). Breast cancer is expected to account for 192,200 new cancer cases in the United States in 2001, and more than 40,000 women are projected to die in 2000 from this disease (1). A variety of molecular alterations have been reported in breast cancer. These include loss of heterozygosity (1p, 3p, 7q, 11p, 17p, 17 and 18q), mutations (BCRA1,2, p53, c-H-ras-1), and/or gene amplifications (c-myc, c-erbB-2) (80, 35, 36, 60, 66, 70, 82, and 56). In the case of c-erbB-2, overexpression has been correlated with aggressive disease and decreased patient survival. Furthermore, anti-erbB-2 antibodies can suppress breast cancer cell growth in vitro and decrease tumor burden in vivo, thereby prolonging patient survival (91, 43, 6, and 77).

To date a ligand that binds to c-erbB-2 has not been identified (98, 71). Instead, c-erbB-2 is capable of heterodimerizing with the other members of the EGF receptor family once these receptors bind their ligands (98, 71, 119, and 115). These ligands include epidermal growth factor (EGF), transforming growth factor-alpha (TGF-), heparin-binding EGF-like growth factor (HB-EGF), betacellulin, amphiregulin (AR) and epiregulin. HB-EGF and amphiregulin are heparin-binding factors. In addition, breast cancers overexpress fibroblast growth factor-2 (FGF-2) and type1–4 FGF receptors (11), and hepatocyte growth factor (HGF) and its receptor (c-Met) (bc 19). Both FGF-2 and HGF are heparin-binding factors. Together, these observations suggest that multiple heparin-binding growth factors participate in the pathobiology of breast cancer in humans.

The binding of heparin-binding growth factors to their cell surface receptors often requires the presence of cell-surface heparan sulfate proteoglycans (HSPGs) (20, 22, 23). There are two main families of such molecules, syndecans and glypicans, that differ significantly in core protein domain structure (24, 25). Six members of the glypican family (glypican 1 through 6) and four members of the syndecan family (syndecan 1 through 4) have been reported to date (26–30). They have important functions with respect to cell behavior, including cell-cell and cell-extracellular matrix adhesion 31, 32), grwth factor signaling (24, 34) and protection of growth factors such as FGF-2 from thermal denaturation and proteolytic attack (35, 36). They also regulate the interaction of several heparin-binding growth factors with their receptors and, consequently, their biological activity (37).

SUMMARY OF THE INVENTION

We have discovered that glypican-1 expression-both mRNA and protein—is dramatically up-regulated in human cancers. We have also found that glypican-1 is highly expressed by human pancreatic carcinoma cell lines in vitro, and that in such cells glypicans (and no other classes of HSPGs) are uniquely required for FGF2 and HB-EGF induced mitogenesis in the case of pancreatic cancer and FGF2, HB-EGF and HGF in the case of human breast cancer. Ten of twenty breast cancer samples exhibited moderate to high levels of glypican-1 mRNA. The glypican-3 mRNA transcript was expressed at moderate to high levels in 5 of 20 normal breast tissue samples. In the breast cancers, it was expressed at moderate to high levels in 6 of 20 samples. The glypican-4 mRNA transcripts were below the level of detection in the normal samples, and present at low levels in 7 of 20 breast cancer samples. The 3.4- and 2.6-kb syndecan-1 mRNA transcripts were present at low levels in all 20 normal breast tissue samples. In contrast, in the breast cancers, both syndecan-1 transcripts were expressed at moderate to high levels in 9 of 20 samples. Enzymatic destruction of glypicans blocked the stimulatory effect of completely blocked the stimulatory effect of HB-EGF and FGF-2 in vitro. Together, these results demonstrate that glypican-1 may play a crucial role in the growth factor signaling pathways underlying aggressive human cancer. Transfection of cells with glypican-1 antisense markedly attenuated the growth stimulatory effects of HB-EGF, HRG-α, HRG-β, FGF2 and HGF confirming the importance of glypicans in breast cancer and suggesting the use of antisense or other factors that decrease glypican-1 as therapeutic agents for breast cancer.

We also investigated the effects of a chronic decrease in glypican-1 expression on growth factor responsiveness and in vivo tumorigenicity of PANC-1 human pancreatic cancer cells. We discovered that the stable expression of glypican-1 antisense mRNA in these cells results in reduced glypican-1 protein expression, blockage of the mitogenic response to the heparin-binding growth factors FGF2, HB-EGF, and HGF, and decreased tumorigenicity in vivo.

We have discovered that the glycosylphosphatidylinositol-(GPI-) anchored HSPG glypican-1 is strongly expressed in human breast and pancreatic cancer—both by the cancer cells and in the case of pancreatic cancer the adjacent fibroblasts—whereas expression of glypican-1 is low in the normal pancreas and in chronic pancreatitis. Treatment of two pancreatic cancer cell lines, which express glypican-1, with the enzyme phosphoinositide-specific phospholipase-C (PI-PLC) abrogated their mitogenic responses to two heparin-binding growth factors that are commonly overexpressed in pancreatic cancer: fibroblast growth factor-2 (FGF2) and heparin-binding EGF-like growth °factor (HB-EGF). PI-PLC did not alter the response to the non-heparin binding growth factors EGF and insulin-like growth factor-1 (IGF-1). Treatment of MDA-MB-231 and MDA-MB-468 breast cancer cells with phosphoinositide-specific phospholipase-C (PI-PLC) abrogates the mitogenic response to two heparin-binding growth factors, heparin-binding epidermal growth factor-like growth factor (HB-EGF) and fibroblast growth factor-2 (FGF-2). Syndecan-1 is also expressed at high levels in breast cancer tissues as well as breast cancer cells by comparison with breast normal tissues. However, it is not removed from cell-surface by PI-PLC treatment and clones expressing the glypican-1 antisense did not decrease syndecan-1 levels. Stable expression of a form of glypican-1 engineered to possess a transmembrane domain instead of a GPI-anchor conferred resistance to the inhibitory effects of PI-PLC on growth factor responsiveness in pancreatic and breast cancer cells. Furthermore, temporary or permanent transfection of a glypican-1 antisense construct attenuated glypican-1 protein levels and the mitogenic response to FGF2 and HB-EGF. Thus, glypican-1 plays an essential role in the responses of pancreatic and breast cancer cells, and most likely in other glypican-responsive carcinomas as well, to certain mitogenic stimuli, that it is relatively unique in relation to other HSPGs. Glypican can be used to detect the carcinoma in vitro and therapeutics that either bind to (e.g., antibodies or drugs), remove (e.g., enzymes) or prevent the expression (e.g., antisense constructs) of surface of the extracellular domain of glypican-1 are effective in retarding the growth of glypican-responsive carcinomas such as human breast cancer.

BRIEF DESCRIPTION OF THE DRAWINGS

FIG. 7 shows: A: Expression of the modified glypican-1, glyp1-VSVGTMR, in PANC-1 cells. RNA isolated from wild-type PANC-1 cells, sham-transfected PANC-1 cells, and three pCDNA3.1/glyp1-VSVGTMR clones (20 μg) were subjected to Northern blot analysis using a $^{32}$P-labeled glypican-1 cDNA probe (500,000 cpm/ml). Exposure time was 12 h. Low levels of the endogenous glypican-1 transcript (3.5 kb) are seen in all cells. High levels of the glyp1-VSVGTMR transcript (2.5 kb) are seen only in the transfected clones. B: Immunoblot analysis using an anti c-myc antibody recognizing the c-myc-epitope of the glyp1-VSVGTMR construct confirmed protein expression of glyp1-VSVGTMR in the transfected clones.

A: Immunostaining did not yield any glypican-1 immunoreactivity in the connective tissue cells or in the terminal ductal-lobular unit; and B: In situ hybridization analysis of serial section did not yield any specific signals. Magnification, ×200.

Figure 30:
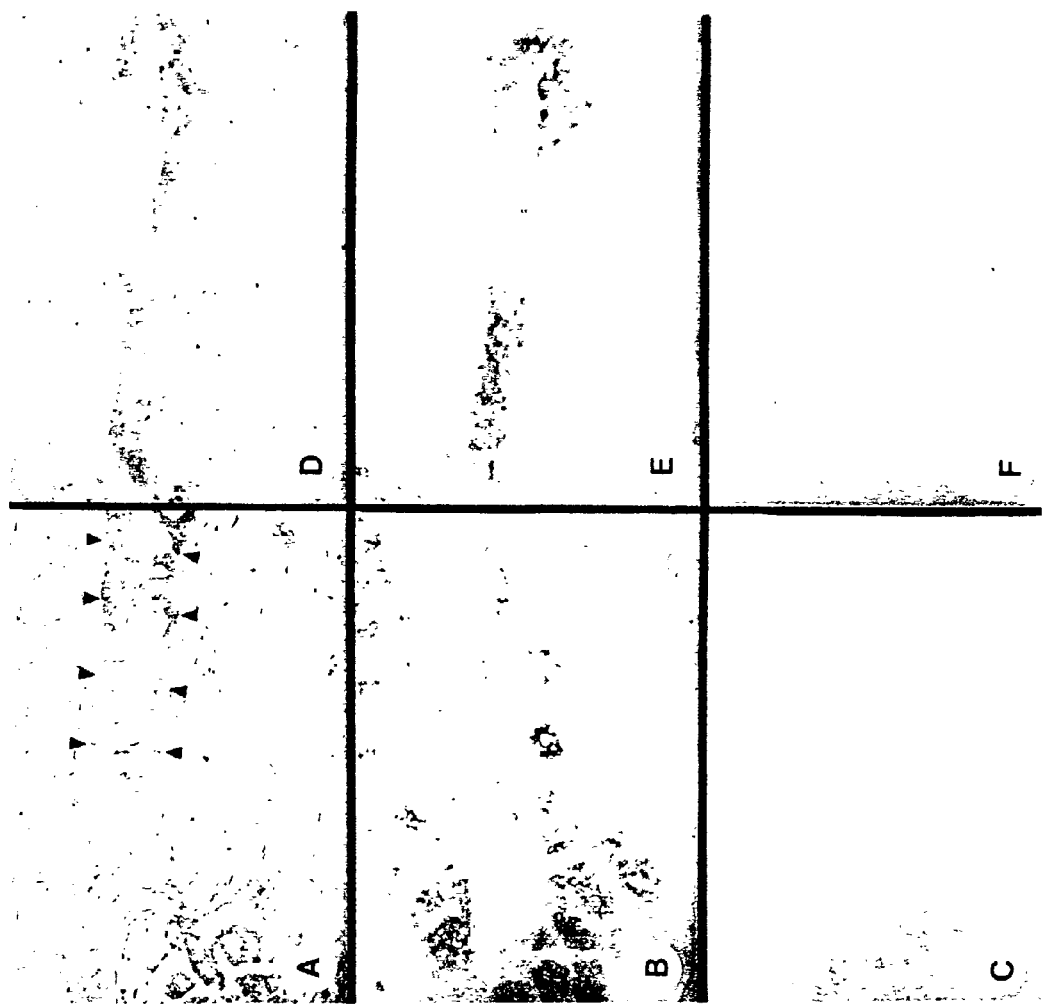

FIG. 30 show glypican-1 localization in human breast cancer tissue:

A: Immunostaining revealed moderate to strong glypican-1 immunoreactivity in the intraductal carcinomas and adjacent fibroblasts;

B: In situ hybridization analysis of serial sections revealed a moderate to strong glypican-1 mRNA signal in the small cancer cells that had a lobualr architecture;

D: H&E-stained section;

E: In situ hybridization analysis of serial sections revealed a moderate glypican-1 mRNA signal in the cancer cells; and C, F: Hybridization with the glypican-1 sense probe did not yield any specific signals. Magnification, ×200.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an inventive use of glypican-1 and agents binding to and suppressing expression of glypican-1 for detection and therapy of human carcinomas.

(1) MATERIALS AND METHODS

Materials

The following materials were purchased: FBS, DMEM and RPMI medium Leibovitz's medium, trypsin solution, penicillin-streptomycin solution, and Geneticin (G418) from Irvine Scientific (Santa Ana, Calif.); Genescreen membranes from New England Nuclear (Boston, Mass.); restriction enzymes, pMH6 vector, the random primed labeling kit, the Genius 3 non-radioactive nucleic acid detection kit, and the Genius 4 RNA labeling kit from Boehringer-Mannheim (Indianapolis, Ind.); phosphoinositide-specific phospholipase-C (PI-PLC) from Oxford Glycosciences Inc. (Bedford, Mass.); Sequenase version 1.0 DNA Sequencing from USB Specialty Biochemicals(Cleveland, OH); [α-$^{32}$P]dCTP, [α-$^{32}$P]CTP, [γ-$^{35}$S]dATP from Amersham (Arlington Heights, Ill.); DNA molecular weight markers, and Lipofectamine from GIBCO BRL (Gaithersburg, Md.); NBT/BCIP Stock Solution from Roche Molecular Biochemical (Indianapolis, Ind.); monoclonal mouse anti-CD138 (Syndecan-1) antibody from Serotec Inc. (Raleigh, N.C.);Anti-c-myc (9E10), anti ERK-1, and horseradish-peroxidase conjugated anti-rabbit antibodies from Santa Cruz Biotechnology, Inc. (Santa Cruz, Calif.); Cy3-conjugated anti-rabbit IgG antibodies from Jackson ImmunoResearch (West Grove, Pa.); pBluescript-IISK+ from Stratagene (La Jolla, Calif.); DEAE-Sephacel from Pharmacia Biotech (Piscataway, N.J.); enhanced chemiluminescence (ECL) blotting kit from Pierce (Rockford, Ill.); pCDNA 3.1 Myc-His from Invitrogen (Carlsbad, Calif.); Centriprep Concentrators from Amicon (Beverly, Mass.); Lab-Tek Chamber Slides from Nunc Inc. (Naperville, Ill.); Adult and Fetal Human Multiple Tissue Northern Blots from Clontech (Palo Alto, Calif.); Heparitinase (Heparinase III), HRG-α, HRG-β and HGF from R&D Systems (Minneapolis, Minn.) and all other reagents from Sigma (St. Louis, Mo.). PANC-1, MIA-PaCa-2, ASPC-1, CAPAN-1 human pancreatic cell lines were obtained from ATCC (Rockville, Md.). COLO-357 and T3M4 human pancreatic cell lines were a gift from Dr. RS Metzger (Durham, N.C.). Recombinant human EGF was from Chemicon Inc. (Temecula, Calif.); recombinant human HGF was a gift from Dr. J. S. Rubin at the NIH; recombinant human IGF-1 was a gift from Genentech (South San Francisco, Calif.). Human recombinant EGF was a gift from Chiron Inc. (Emmeryville, Calif.). Human recombinant HB-EGF (residues 73–149 of mature human HB-EGF) and human recombinant FGF-2 were gifts from Dr. J. Abraham at Scios Nova Inc. (Mountain View, Calif.). IGF-1 was a gift from Genentech Inc. (South San Francisco, Calif.). MDA-MB-231 and MDA-MB-468 human breast cancer cell lines were obtained from American Type Culture Collection (Manassas, Va.).

Tissue Samples

Normal human pancreatic tissue samples (7 male, 5 female donors; median age 41.8 years; range 14–68 years), chronic pancreatitis tissues (13 male, 1 female; median age 42.1 years; range 30–56 years), and pancreatic cancer tissues (10 male, 6 female; median age 62.6 years; range 53–83 years) were obtained through an organ donor program and from surgical specimens obtained from patients with severe symptomatic chronic pancreatitis or from pancreatic cancer patients. According to the TNM classification of the Union Internationale Contre le Cancer (UICC) 6 tumors were stage 1, 1 stage 2, and 9 stage 3 ductal cell adenocarcinoma. Freshly removed tissue samples were fixed in 10% formaldehyde solution for 12–24 h and paraffin-embedded for histological analysis. In addition, tissue samples were frozen in liquid nitrogen immediately upon surgical removal and maintained in −80° C. until use for RNA extraction. All studies were approved by the Ethics Committee of the University of Bern and by the Human Subjects Committee at the University of California, Irvine.

Breast cancer tissues (20 female patients; median age: 60.8 yr; range: 38–76 yr) were obtained from surgical specimens from patients with breast cancer. Normal human breast tissue samples (10 female patients; median age: 63.2 yr; range: 38–76 yr) were obtained from the same mastectomy samples, but at a distance of at least 5 cm from the cancer area. According to the TNM classification of the Union Internationale Contre le Cancer (UICC), 10 tumors were stage 1, 7 tumors were stage 2 and 3 tumors were stage 3 breast carcinoma. Freshly removed tissue samples were fixed in 10% formaldehyde solution for 12–24 h and paraffin embedded for histological analysis. In addition, tissue samples were frozen in liquid nitrogen immediately upon surgical removal and maintained in −80° C. until used for RNA extraction. All studies were approved by the Ethics Committee of the Yamanashi-Medical University and by the Human Subjects Committee at the University of California, Irvine.

Construction of Vectors

A 599 bp human glypican cDNA probe (nucleotides 920–1518) was isolated as described previously (63) and subcloned into Bluescript-IISK+ vector. For in situ hybridization, a 210 bp cDNA fragment (nucleotides 1280-1489) of human glypican was subcloned into Bluescript-IISK+ vector. Authenticity was confirmed by sequencing. Glypican-2 and glypican-5 constructs were prepared as described previously (108, 97). A 239 bp human glypican-3 cDNA fragment, corresponding to nt 927 to 1165 of the human glypican-3 cDNA sequence (Genbank: HSU50410), and a 273 bp human glypican-4 cDNA fragment, corresponding to nt 12 to 284 of a human glypican-4 EST sequence (Genbank: AA046130) were generated by RT-PCR from human placenta RNA. A glypican-1 antisense construct was prepared by RT-PCR amplification of human placenta cDNA as described previously (90). Briefly, the 1751 bp fragment (nt 123–1873; Genbank accession X54232), that covered from 100 bp downstream of the start codon to 25 bp downstream of the end of the coding region, was subcloned in the antisense orientation into the pMH expression vector. The primers used for the glypican-3/-4 preparation contained a EcoRI and BamHI site, respectively, attached to the 5'-end and preceded by a 3 bp overhang. Glypican-3 sense: 5'-AGT-GGATCC-CTGCTCTTACTGCCAGGGAC SEQ ID NO: 1, antisense: 5'-GTA-GAATTC-GCTTTCCTGCAT-TCTTCTGG. SEQ ID NO: 2 Glypican-4 sense: 5'-AGT-GGATCC-GTTGACACCAGCAAACCAGA SEQ ID NO:3, antisense: 5'-GTA-GAATTC-AGTGAGGAGGTAG-GCCTGTG SEQ ID NO: 4. Authenticity was confirmed by sequencing. An eukaryotic expression vector that directs expression of a transmembrane version of glypican-1 was constructed by fusing the membrane domain of the vesicular stomatitis virus glycoprotein (VSVG) (1) with the extracellular domain of glypican-1. Briefly, a 80 bp fragment encoding the transmembrane domain of VSVG (VSVGTMR) was amplified using the primers sense: 5'GCCACGTGTCCAT-TGCCTCTTTTC SEQ ID NO: 5 and antisense: 5' GCTCTAGACTAAAGCTTGAGAACCAA SEQ ID NO: 6, digested with EcoRI and XbaI, and subcloned into the pCDNA3.1-myc-His expression vector. Next, a BamHI-PmII 1.7 kb fragment, corresponding to the extracellular domain of the rat glypican-1 was inserted into the pCDNA3.1-myc-His [VSVGTMR] expression vector by directional cloning. The construct was termed glyp1-VS-VGTMR. Authenticity was confirmed by sequencing. The final result contained aminoacids 1–539 of rat glypican-1 followed by HVSIASFFFIIGLIIGLFVVLKLSRGPFE QKLISEEDLNMHTGHHHHHH SEQ ID NO: 1. A glypican-1 antisense construct was prepared by PCR amplification of human placenta cDNA. The 1751 bp fragment (nt 123–1873), which covered from 100 bp downstream of the start codon to 25 bp downstream of the end of the coding region, was subcloned in the antisense orientation into the pMH6 expression vector. The primers used for the glypican-1 preparation contained a EcoRI and HindIII site, respectively, attached to the 5'-end and preceded by a 3 bp overhang. Sense: 5'-GTA-GAATTC-GGACCTTGGCTCT-GCCCTTC SEQ ID NO: 8, antisense: 5'-AGT-AAGCTT-GTAAGGGCCAGGAAGAGGAG SEQ ID NO: 9. The construct was termed G1-AS-1751. A 400-bp human syndecan-1 cDNA probe (nucleotide [nt] 502–902) was isolated and subcloned into Bluescript-IISK+ vector.Authenticity was confirmed by sequencing.

RNA Extraction and Northern Blot Analysis

Total RNA was extracted by the single step acid guanidinium thiocyanate phenol chloroform method. RNA was size fractionated on 1.2% agarose/1.8 M formaldehyde gels, electrotransferred onto nylon membranes and cross-linked by UV irradiation. Blots were pre-hybridized and hybridized with cDNA probes or riboprobes and washed under high stringency conditions as previously reported (46). Blots were then exposed at −80° C. to Kodak (Eastman Kodak, Rochester, N.Y.) XAR-5 films and the resulting autoradiographs were scanned to quantify the intensity of the radiographic bands. A BamHI 190 bp fragment of mouse 7S cDNA that cross hybridizes with human cytoplasmatic RNA was used to confirm equal RNA loading and transfer (46).

Immunohistochemistry

A highly specific affinity-purified rabbit anti-rat glypican-1 antibody (64) that also recognizes human glypican-1 was utilized for immunohistochemistry. Paraffin-embedded sections (4 μm) from pancreatic cancer or breast cancer, chronic pancreatitis, normal breast and normal pancreatic tissues were subjected to immunostaining using the sireptavidin-peroxidase technique (Kirkegaad & Perry Laboratories Inc., Gaitherburg, Md.). Endogenous peroxidase activity was blocked by incubation for 30 min with 0.3% hydrogen peroxide in methanol. Tissue sections were incubated for 15 min (room temperature) with 10% normal goat serum and then incubated for 16 h at 4° C. with glypican antibody (2.5 μg/ml) in PBS containing 1% bovine serum albumin (BSA). Bound antibodies were detected with biotinylated goat anti-rabbit IgG secondary antibodies and streptavidin-peroxidase complex, using diaminobenzidine tetrahydrochloride as the substrate. Sections were counter-stained with Mayer's hematoxylin. Sections incubated with non-immune rabbit IgG or without primary antibodies did not yield positive immunoreactivity. Furthermore, preabsorption of the anti-glypican-1 antibody with the glypican-1 peptide to which the antibody had been raised completely abolished immunoreactivity.

Immunoblotting

Cells were washed with PBS (4° C.) and solubilized in lysis buffer containing 50 mM Tris-Hcl, pH 7.4, 150 mM NaCl, 1 mM EDTA, 1 μg/ml pepstatin A, 1 mM phenylmethylsulfonyl fluoride (PMSF), and 1% Triton X-100. Digestion with heparitinase (1 U/ml) was performed in a volume of 30 μl at 37° C. for 6 h and terminated by the addition of 7.5 μl 5×SDS sample buffer and heating at 95° C. for 10 min. For preparation of membranes, cells or tissue samples were homogenized in 20 mM Hepes pH 7.4, 1.5 mM $MgCl_2$, 1 mM EGTA, 1 mM PMSF, 2 mM benzamidine and centrifuged at 1500 g for 10 min. Supernatants were collected and centrifuged at 25,000 g for 30 min. Pellets were resuspended in 20 mM Hepes pH 7.4 containing 10 mM leupeptin. For reduction and alkylation with iodoacetamide, protein lysates were incubated at 95° C. for 4 min in the presence of 10 mM DTT. prior to the addition of iodoacetamide (50 mM final concentration). Samples were incubated at 95° C. for 2 min. For syndecan-1 (40), total lysates were brought to 6 M urea and 50 mM sodium acetate, pH 4.5. They were boiled for 10 min and centrifuged to remove cell debris. DEAE-Sepharose beads were added to the supernatants, and the mixtures were rotated overnight at 4° C. The DEAE beads were washed with PBS containing 0.1% Triton X-100, the bound proteoglycans eluted from the beads with 1 M NaCl in PBS containing 0.1% Triton X-100, and were then diluted with 20 mM Tris, pH 7.0, containing 5 mM $CaCl_2$ to a final concentration of 0.1 M NaCl. For syndecan-1 digestion with chondroitinase ABC (0.2 U/sample) was performed at 37° C. for 2 h and terminated by the addition of 5×SDS sample buffer and heating at 95° C. for 10 min, subjected to SDS-PAGE and transferred to Immobilon P membranes.

Membranes were incubated for 90 minutes with a polyclonal rabbit anti-rat glypican-1 (250 ng/ml) antibody, washed and incubated with a secondary antibody against rabbit IgG for 60 min. After washing, visualization was performed by enhanced chemiluminescence.

Glypican-1 and Syndecan-1 Purification

GAG-containing forms of glypican-1 and syndecan-1 were purified by anion exchange chromatography on DEAE-Sephacel equilibrated in buffer A (50 mM Tris-HCl, pH 8.0, 0.15 M NaCl, 0.1% Triton X-100), as previously reported (36). Cell lysates in buffer B (50 mM Tris-HCl, pH 8.0, 0.15 M NaCl, 0.1% Triton X-100, 1 mM EDTA, 1 µg/ml pepstatin A, 1 mM PMSF) were loaded directly onto columns containing the gel, using column volumes of 0.5 ml of packed gel per milligram protein. Columns were eluted stepwise with buffer A, buffer C (50 mM Tris-HCl, pH 8.0, 0.25 M NaCl, 0.1% Triton X-100), buffer D (50 mM Tris-HCl pH 8.0, 6 M urea, 0.25 M NaCl, 0.1% Triton X-100), and buffer E (50 mM sodium formate, pH 3.5, 6 M urea, 0.2 M NaCl, 0.1% Triton X-100). After restoring the pH with 50 mM Tris-HCl, pH 8.0, 0.1% Triton X-100, gypican-1 or syndecan-1 was eluted from the column with buffer F (50 mM Tris-HCl, pH 8.0, 0.75 M NaCl, 0.1% Triton X-100). The eluted material was diluted fivefold with 50 mM Tris, pH 8.0, 0.1% Triton X-100, concentrated, and clarified by filtration (36). Samples were then resuspended in buffer B and analyzed by immunoblotting.

In Situ Hybridization

To carry out in situ hybridization, tissue sections (4-µm thick) were placed on 3-aminopropyl-methoxysilane-coated slides, deparaffinized, and incubated at room temperature for 20 min with 0.2 N HCl and for 15 min with 50 µg/ml proteinase K at 37° C. (36, 39). The sections were then postfixed for 5 min in PBS containing 4% paraformaldehyde and incucated briefly twice with PBS containing 2 mg/ml glycine and once in 50% (vol/vol) formamide/2×SSC for 1 h before initiation of the hybridization reaction by the addition of 100 µl of hybridization buffer. The hybridization buffer contained 0.6 M NaCl, 1 mM EDTA, 10 mM Tris-HCl (pH 7.6), 0.25% SDS, 200 µg/ml yeast tRNA, 1×Denhard's solution, 10% dextran sulfate, 40% formamide, and 100 ng/ml of the indicated digoxigenin-labeled riborobe (36, 39). Hybridization was performed in a moist chamber for 18 h at 42° C. The sections were then washed sequentially with 50% formamide/2×SSC for 30 min at 42° C., 2×SSC for 20 min at 42° C., and 0.2×SSC for 20 min at 42° C. For immunological detection, the Genius 3 nonradioactive nucleic acid detection kit was used as previously reported (36), using a 1:2000 dilution of alkaline phosphatase-conjugated polyclonal sheep antidigoxigenin Fab fragment antibody. Sections were incubated with NBT/BCIP solution in a dark box for 3 h. After the reaction was stopped with TE buffer (10 mM Tris-HCl, pH 8.0, 1 mM EDTA), the sections were mounted in aqueous mounting medium.

Cell Culture and Growth Assay

Human pancreatic cancer cells were routinely grown in DMEM (COLO-357, MIA-PaCa-2, PANC-1) or RPMI (ASPC-1, CAPAN-1, T3M4) supplemented with 10% FBS, 100 U/ml penicillin, and 100 µg/ml streptomycin (complete medium). To perform growth assays, COLO-357 and PANC-1 cells were plated overnight at a density of 10,000 cells/well in 96-well plates, washed in Hank's buffered saline solution (HBSS), and subsequently incubated in serum-free medium (DMEM containing 0.1% BSA, 5 µg/ml transferrin, 5 ng/ml sodium selenite, and antibiotics) in the absence or presence of various growth factors. For experiments with PI-PLC, cells were incubated with the indicated concentrations of PI-PLC for one hour. Subsequently, the medium was removed and serum-free medium supplemented with PI-PLC and growth factors were added. Incubations were continued for the indicated time prior to adding 3-(4,5-methylthiazol-2-yl)-2,5-diphenyl-tetrazolium bromide (MTT, 62.5 µg/well) for 4 h (86). Cellular MTT was solubilized with acidic isopropanol and optical density was measured at 570 nm with an ELISA plate reader (Molecular Devices, Menlo Park, Calif.). In pancreatic cancer cells the results of the MTT assay correlate with results obtained by cell counting with a hemocymeter and by monitoring $[^3H]$-thymidine incorporation (86, 3).

Human breast cancer cells were routinely grown in Leibovitz's Medium supplemented with 10% FBS, 100 U/ml penicillin, and 100 µg/ml streptomycin (complete medium). To perform growth assays, MDA-MB-231 and MDA-MB-468 were plated overnight at a density of 10000 cells/well in 96-well plates, washed in HBSS, and subsequently incubated in serum-free medium (Leibovitz's Medium containing 0.1% BSA, 5 µg/ml transferrin, 5 ng/ml sodium selenite and antibodies) in the absence or presence of various growth factors. For experiments with PI-PLC, cells were incubated with the indicated concentrations of PI-PLC for 1 hour. Subsequently, the medium was removed and serum-free medium supplemented with PI-PLC and growth factors was added. Incubations were continued for 48 h before adding 3-(4,5-methylthiazol-2-yl)-2,5-diphenyl-tetrazolium bromide (MTT; 62.5 µg/well) for 4 h (38). Cellular MTT was solubilized with acidic isopropanol and optical density was measured at 570 nm with an ELISA plate reader (Molecular Devices, Menlo Park, Calif.). The MTT results correlated with counts obtained by counting cells with a hemocytometer.

Transient and Stable Transfections

Transient transfection of the glypican-1 antisense construct pMH6/G1-AS-1750 and stable transfection of G1-AS-1751 were carried out by the lipofectamine method. 24 h after transfection, cells were plated in 96-well plates for growth assays as described earlier. Stable transfection of pCDNA3.1/glyp1-VSVGTMR into PANC-1 cells was also performed using the lipofectamine method. After reaching confluence, cells were split 1:10 into selection medium (complete medium supplemented with 1 mg/ml G418) and single clones were isolated after 2–4 weeks. After expansion, cells from each individual clone were screened for expression of glypican-1 by Northern and Western blot analysis. Parental PANC-1 cells were also transfected with an empty expression vector carrying the neomycin-resistance gene as a control. Positive clones were routinely grown in selection medium.

For breast cancer stable transfection of G1-AS-1751 into MDA-MB-231 and MDA-MB-468 cells was performed using the lipofection method as described previously (33). Briefly, after reaching confluence, cells were split 1:10 into selection medium (complete medium supplemented with 1.5 mg/ml G418 on MDA-MB-231 and 0.5 mg/ml G418 on MDA-MB-468) and single clones were isolated after 3–4 weeks. After expansion of individual clones, cells from each individual clone were screened for expression of glypican-1 sense and antisense mRNA by Northern blot analysis and for glypican-1 protein expression by immunoblotting. Parental MDA-MB-231 and MDA-MB-468 cells were also transfected with an empty expression vector carrying the neomycin-resistance gene as a control. Positive clones were routinely grown in selection medium.

Immunofluorescence

Cells were plated at a density of 100,000 cells/slide on culture chamber slides and incubated for 24 h in complete medium. Subsequently, cells were incubated for 1 h in serum free medium in the absence or presence of PI-PLC (0.5 U/ml), washed, and incubated for 30 min at room temperature in DMEM containing 5% goat serum, 5% fetal bovine serum, and 10 mM Hepes pH 7.5. All antibody dilutions and washings were carried out at 4° C. using this solution. Slides were then incubated for 60 min with the rabbit anti-rat glypican-1 antibody (2.5 μg/ml), washed and incubated with a Cy3-conjugated antibody against rabbit IgG for 60 min. Cells were then washed, fixed, and prepared for immunofluorescence microscopy.

Statistics

Student's t-test was used for statistical analysis of the experiments. $p<0.05$ was taken as the level of significance. Results of MTT cell growth assays are expressed as mean ±standard error of mean (SEM) of at least three separate experiments.

Growth in Nude Mice

Parental, sham transfected or glypican-1 antisense transfected PANC-1 ($1\times10^6$) cells were injected subcutaneously into 2 sides of 4–6 weeks old, female, athymic (nude) mice. The animals were monitored for tumor formation every week for 8 weeks. Tumor volume was calculated as $\pi/4\times$ width×height×length of the tumor (47).

(2) RESULTS

Glypican-1 Expression in Human Pancreatic Tissue

Figure 1:
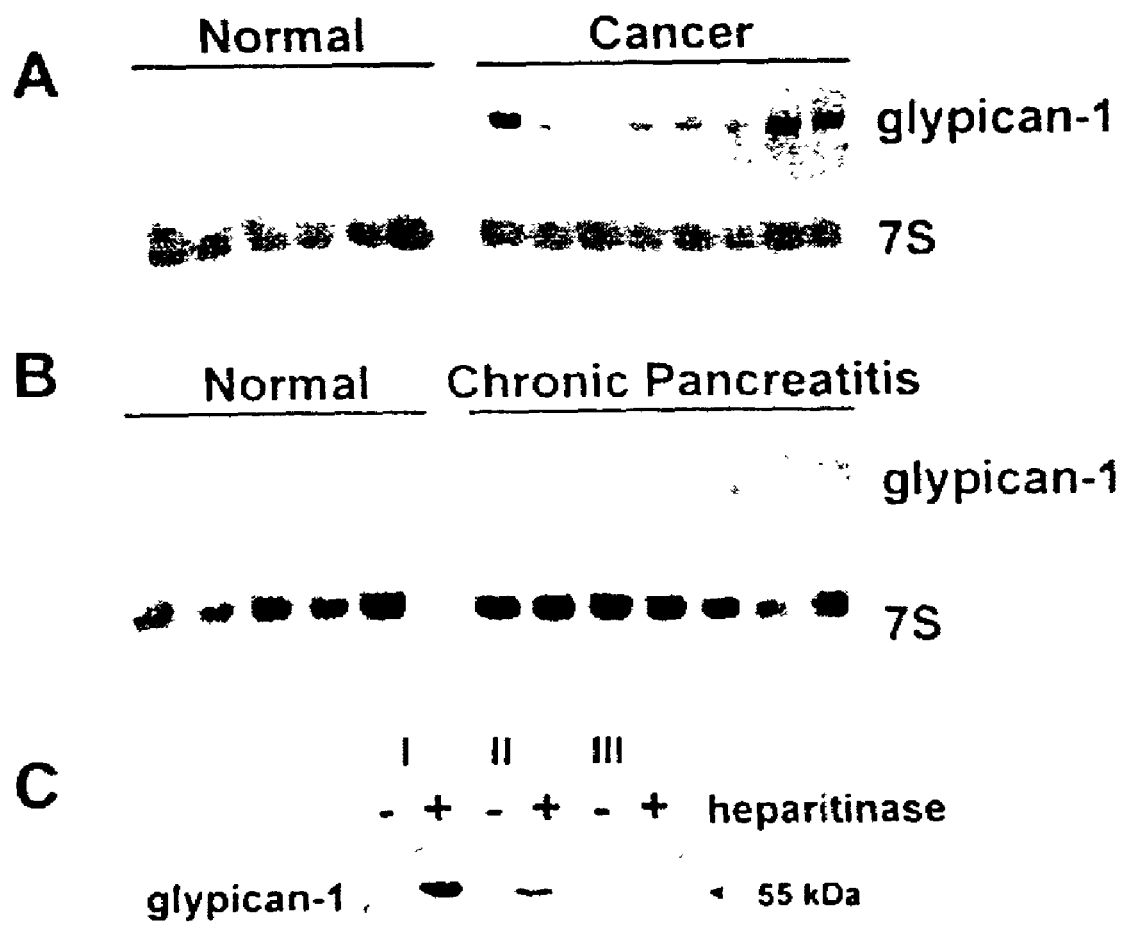
FIG. 1 shows expression of glypican-1 in pancreatic tissues. Total RNA (20 µg/lane) from 6 normal pancreatic tissues, and 8 pancreatic cancers (A), and from five normal and seven chronic pancreatitis tissues (B) were subjected to Northern blot analysis using a $^{32}$P-labeled glypican-1 cDNA probe (500,000 cpm/ml). A 7S ribosomal cDNA probe (50,000 cpm/ml) was used as a loading and transfer control. Exposure times were 2 days for glypican-1 and 6 h for 7S. C: glypican-1 protein expression in pancreatic cancers. Membrane preparations (30 µg/lane) from 3 pancreatic cancer tissue samples were incubated in the absence (−) or presence (+) of heparitinase for 6 h at 37° C. Western blotting was carried out with an affinity purified rabbit anti-rat glypican-1 antibody (250 ng/ml).
Figure 2:
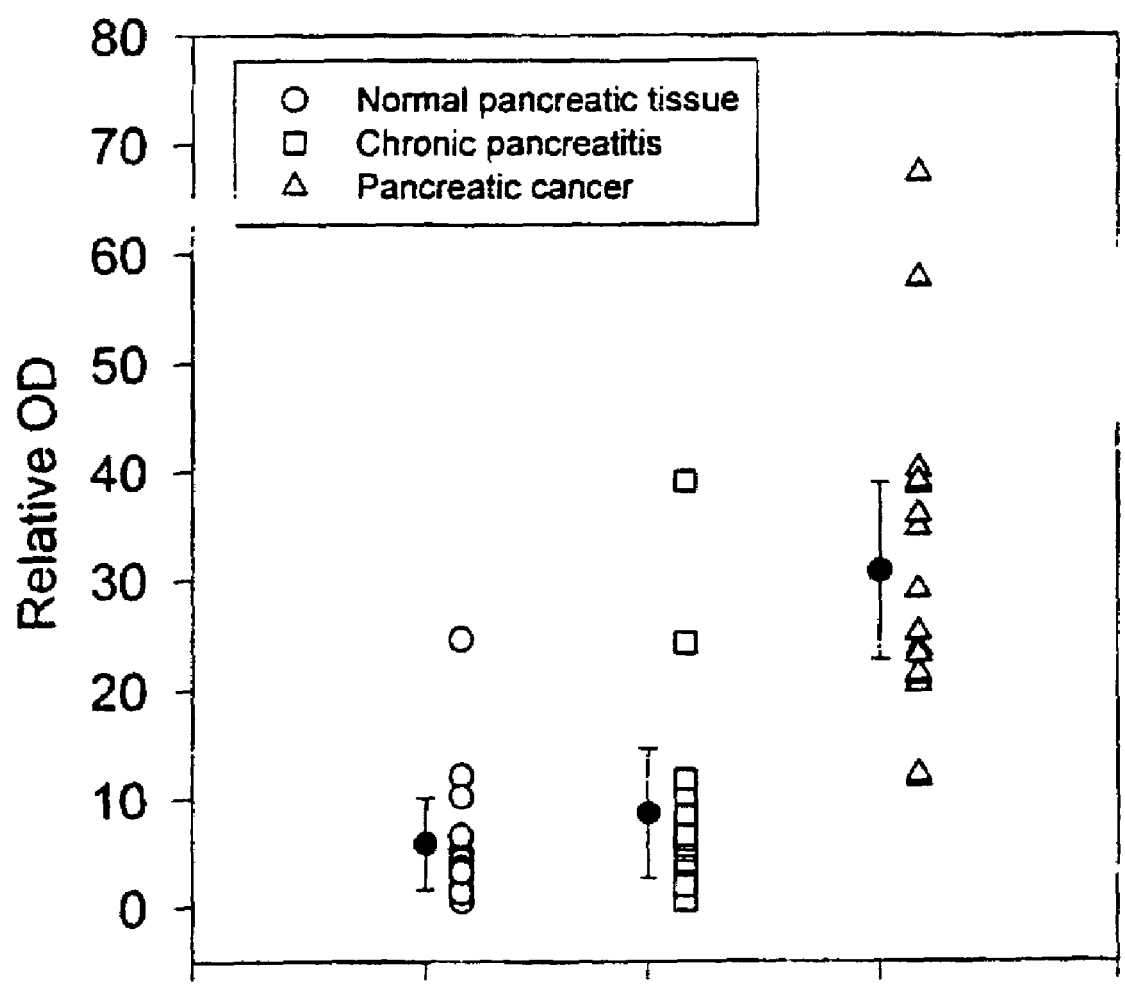
FIG. 2 shows relative expression of glypican-1 mRNA. Autoradiographs of Northern blots for glypican-1 and 7S RNA from 12 normal (○), 14 chronic pancreatitis (□), and 16 cancerous (ρ) pancreatic tissue samples were analyzed by densitometry and the level of glypican-1 expression was calculated as the ratio of glypican-1 and 7S RNA. Data are expressed as median glypican-1 scores (●)±SD. The median glypican-1 score of the cancer samples was significantly greater than the medians from normal and chronic pancreatitis tissues ($p<0.01$).

Northern blot analysis was performed on total RNA isolated from 12 normal pancreatic tissues, 16 pancreatic cancers, and 14 chronic pancreatitis samples. The 3.7 kb glypican-1 mRNA transcript was of relatively low abundance but clearly visible in 4 of 12 normal pancreatic tissue samples (FIG. 1A) and in 3 of 14 chronic pancreatitis samples. It was also faintly visible on the original autoradiographs in 7 normal and 9 chronic pancreatitis samples (FIG. 1B). In contrast, 12 of 16 pancreatic cancer samples exhibited moderate to high levels of glypican-1 mRNA (FIG. 1A). Densitometric analysis of all the autoradiograms indicated that by comparison with normal pancreatic tissues there was an 8-fold increase ($p<0.01$) in glypican-1 mRNA levels in the pancreatic cancer samples (FIG. 2). In contrast, glypican-1 mRNA levels were similar in chronic pancreatitis and normal pancreatic samples.

To determine whether glypican-1 protein levels were also elevated in pancreatic cancer, immunoblotting was carried out using a highly specific anti-glypican-1 antibody. Intact HSPGs, including glypican-1, generally appear on immunoblots as broad high-molecular-weight smears having faint immunostaining, in part due to poor binding of proteoglycans to blotting membranes (38, 64, 87). However, following digestion with heparitinase, HSPGs migrate as distinct bands on SDS-PAGE. Therefore, membrane preparations from normal and cancerous pancreatic tissue (30 μg) were incubated in the absence or presence of heparitinase for 6 h at 37° C. and subjected to SDS-PAGE followed by Western blot analysis. A single 55 kDa band corresponding to the glypican-1 core protein was seen in 4 of 6 pancreatic cancer samples following heparitinase digestion, but not in untreated samples. In contrast, membrane preparations from 4 normal pancreatic tissues did not exhibit a glypican-1 band even following heparitinase treatment. An example of an immunoblot experiment with pancreatic cancer tissues is shown in FIG. 1C.

Figure 27:
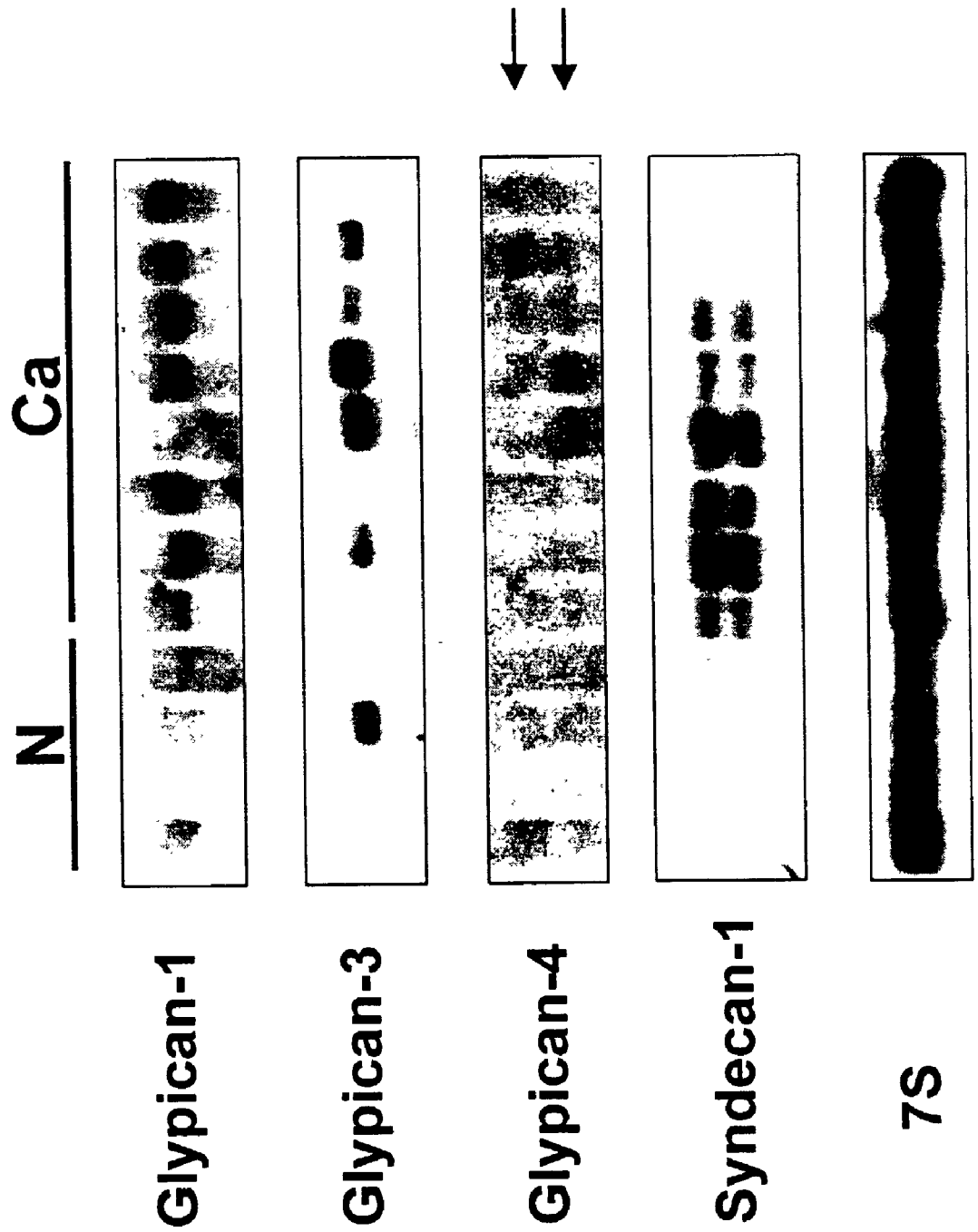
FIG. 27 shows a Northern blot analysis of glypicans and syndecan-1 in breast tissues. Total RNA (20 μg/lane) from four normal breast tissues (N) and eight breast cancers (Ca) were subjected to Northern blot analysis using a $^{32}$P-labeled glypican-1, -3, -4 and syndecan-1 cDNA probes (500,000 cpm/ml). A 7S ribosomal cDNA probe (50,000 cpm/ml) was used as a loading and transfer control. Exposure times were 1 day for glypican-1, -3 and syndecan-1, 2 days for glypican-4 and 6 hours for 7S. Arrows indicate the two glypican-4 mRNA transcripts (3.4 and 4.6 kb).
Figure 28:
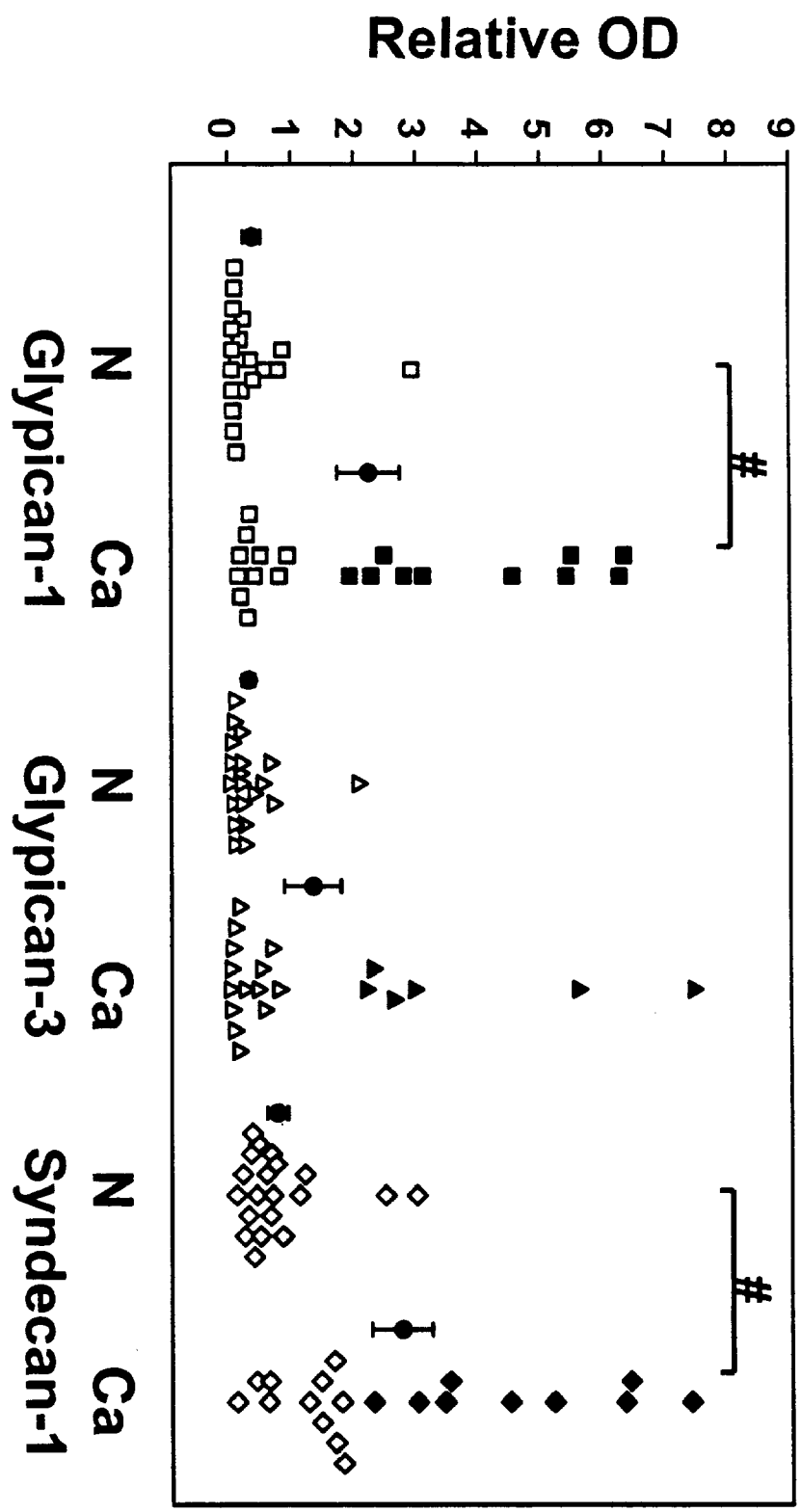
FIG. 28 Relative expression of glypican-1, glypican-3 and syndecan-1 mRNA. Autoradiographs of Northern blots for glypican-1, glypican-3, syndecan-1 and 7S RNA from 20 normal and 20 cancerous breast tissue samples were analyzed by densitometry and the level of glypican-1, glypican-3 or syndecan-1 expression was calculated as the ratio of glypican-1 (square), glypican-3 (triangle) or syndecan-1 (diamond) and the corresponding 7S RNA. Closed symbols represent high expressing groups of breast cancer tissues for glypican-1 (■), glypican-3 (▲) and syndecan-1 (♦). Data are expressed as mean scores ±SD. The mean glypican-1 and syndecan-1 scores of the cancerous samples were significantly greater than the respective mean values from normal breast tissue samples (#:p<0.005).

Expression of Members of the Glypican Family and Syndecan-1 in Human Breast Tissue Northern blot analysis was performed on total RNA isolated from 20 normal breast tissues and 20 breast cancer samples. The 3.7-kb glypican-1 mRNA transcript was of relatively low abundance in 6 of 20 normal breast tissue samples and below the level of detection in the other 14 samples. In contrast, 10 of 20 breast cancer samples exhibited moderate to high levels of glypican-1 mRNA. The glypican-3 mRNA transcript was expressed at moderate to high levels in 5 of 20 normal breast tissue samples. In the breast cancers, it was expressed at moderate to high levels in 6 of 20 samples. The glypican-4 mRNA transcripts were below the level of detection in the normal samples, and present at low levels in 7 of 20 breast cancer samples. The 3.4- and 2.6-kb syndecan-1 mRNA transcripts were present at low levels in all 20 normal breast tissue samples. In contrast, in the breast cancers, both syndecan-1 transcripts were expressed at moderate to high levels in 9 of 20 samples. A representative Northern blot is shown in FIG. 27. Glypican-2 and -5 mRNA transcripts were below the level of detection in both normal and cancer samples. The same cDNAs used in present study are able to detect the presence of the corresponding glypican-2 and -5 mRNA transcripts in human brain RNA (36), indicating that the failure to detect these transcripts in breast tissues was not due to technical difficulties with these cDNAs.

To determine whether syndecans were also expressed at high levels in breast cancer, we next examined the expression of syndecan-1. The 3.4- and 2.6-kb syndecan-1 mRNA transcripts were present at low levels in all 10 normal breast tissue samples. However, with the exception of one sample, both transcripts were only clearly visible on the original autoradiographs. In contrast, in the breast cancers, both syndecan-1 transcripts were expressed at moderate to high levels in 9 of 20 samples (FIG. 1D).

Densitometric analysis of all the autoradiographs indicated that in comparison with normal breast tissues there was a 6.4 fold increase ($p<0.005$) in glypican-1 mRNA levels in the breast cancer tissues (FIG. 2). There was also a 4.0 fold increase in glypican-3 mRNA levels, but this difference failed to achieve statistical significance ($p=0.0583$). However, a subgroup of patients had relatively high levels of glypican-1 (10 cases; $p<0.001$) or glypican-3 (6 cases; $p<0.01$). There was also a 3.5 fold increase ($p<0.005$) in syndecan-1 mRNA levels in the breast cancer samples (FIG. 2). Furthermore, a subgroup of patients had relatively high levels of syndecan-1 (9 cases; $p<0.001$). Interestingly, all 10 tumor samples that exhibited high glypican-1 mRNA levels (FIG. 2, solid squares), also exhibited high syndecan-1 mRNA levels (FIG. 2, solid diamonds). Furthermore, 9 of 10 tumors with stage 2 or 3 disease exhibited high levels of glypican-1 and syndecan-1 by Northern blot analysis. In contrast, low levels of glypican-1 mRNA were only evident in 1 of 10 tumors with stage 2 or 3 disease, but in 9 of 10 tumors with stage 1 disease.

Immunohistochemistry and in situ Hybridization

Figure 3:
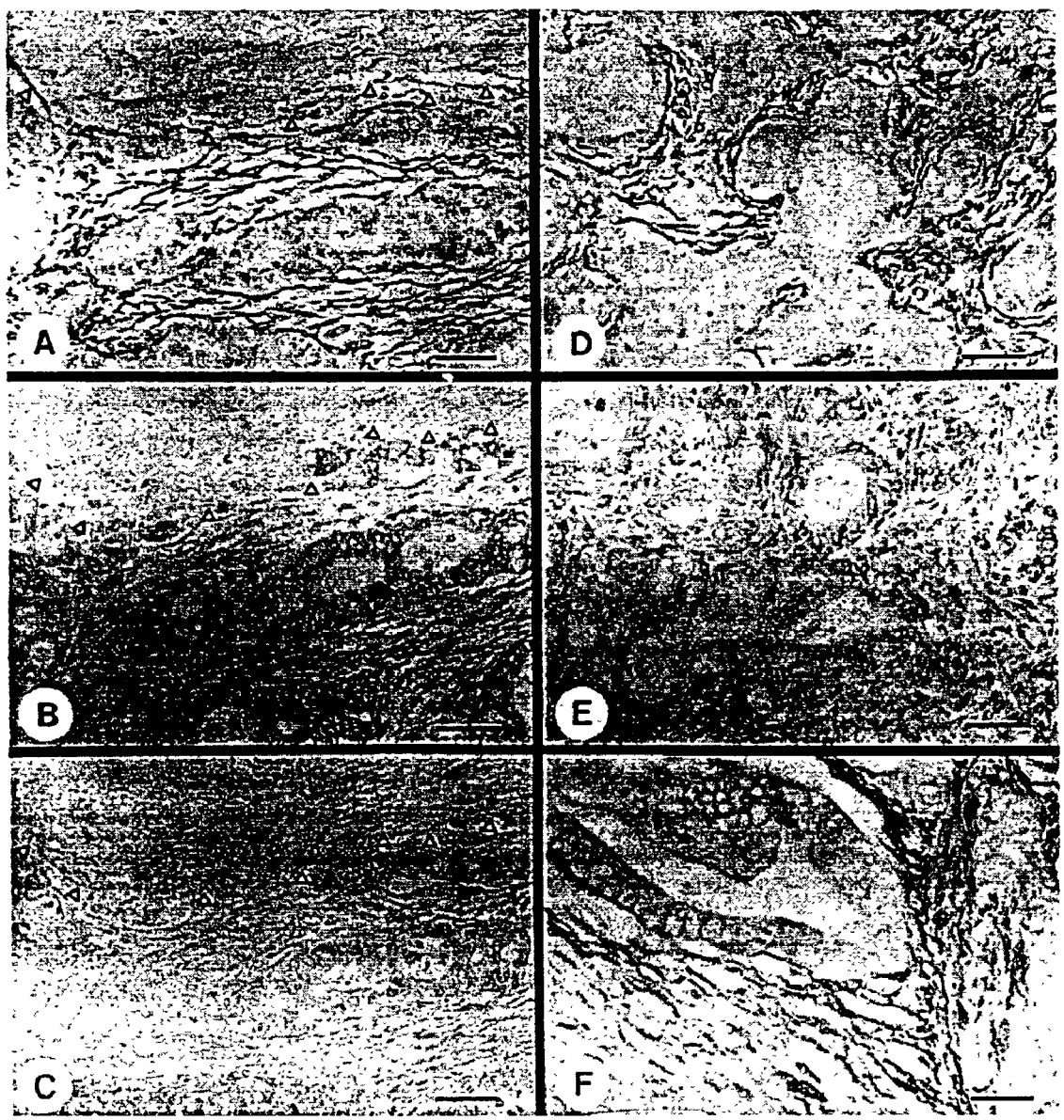
FIG. 3 shows immunohistochemistry and in situ hybridization analysis of glypican-1 expression in human pancreatic cancer. Strong glypican-1 immunoreactivity was present in the fibroblasts surrounding the cancer cells (A,D), but not in the fibroblasts that were more distant from the tumor (A, arrowheads). Strong Glypican-1 mRNA in situ hybridization signals were present in both the cancer cells and in the fibroblasts immediately adjacent to the cancer cells (B,E). In contrast, glypican-1 mRNA expression was not evident in the fibroblasts distant from the tumor (B, arrowheads). In situ hybridization with a glypican-1 sense probe did not reveal any specific signal (C). Panel F provides a high power magnification, revealing faint glypican-1 immunoreactivity in the ductal like cancer cells. Scale bar: 50 µm (A–E), 25 µm (F).

To assess the exact sites of expression of glypican-1, immunohistochemistry and in situ hybridization were carried out. In the normal pancreas and in the pancreas from individuals with chronic pancreatitis, faint to moderate glypican-1 immunoreactivity was present in a few fibroblasts (data not shown). In the pancreatic cancer samples, strong glypican-1 immunoreactivity was present in many fibroblasts that were immediately adjacent to the cancer cells (FIGS. 3A,D). Faint glypican-1 immunoreactivity was also evident in some cancer cells (FIG. 3F). In contrast, by in situ hybridization, glypican-1 mRNA was strongly expressed in both the cancer cells and the adjacent fibroblasts (FIGS. 3B,E). Fibroblasts distant from the cancer cells did not exhibit increased glypican-1 mRNA expression (FIG. 3B). In situ hybridization with sense probes did not produce any specific signal (FIG. 3C).

Figure 18:
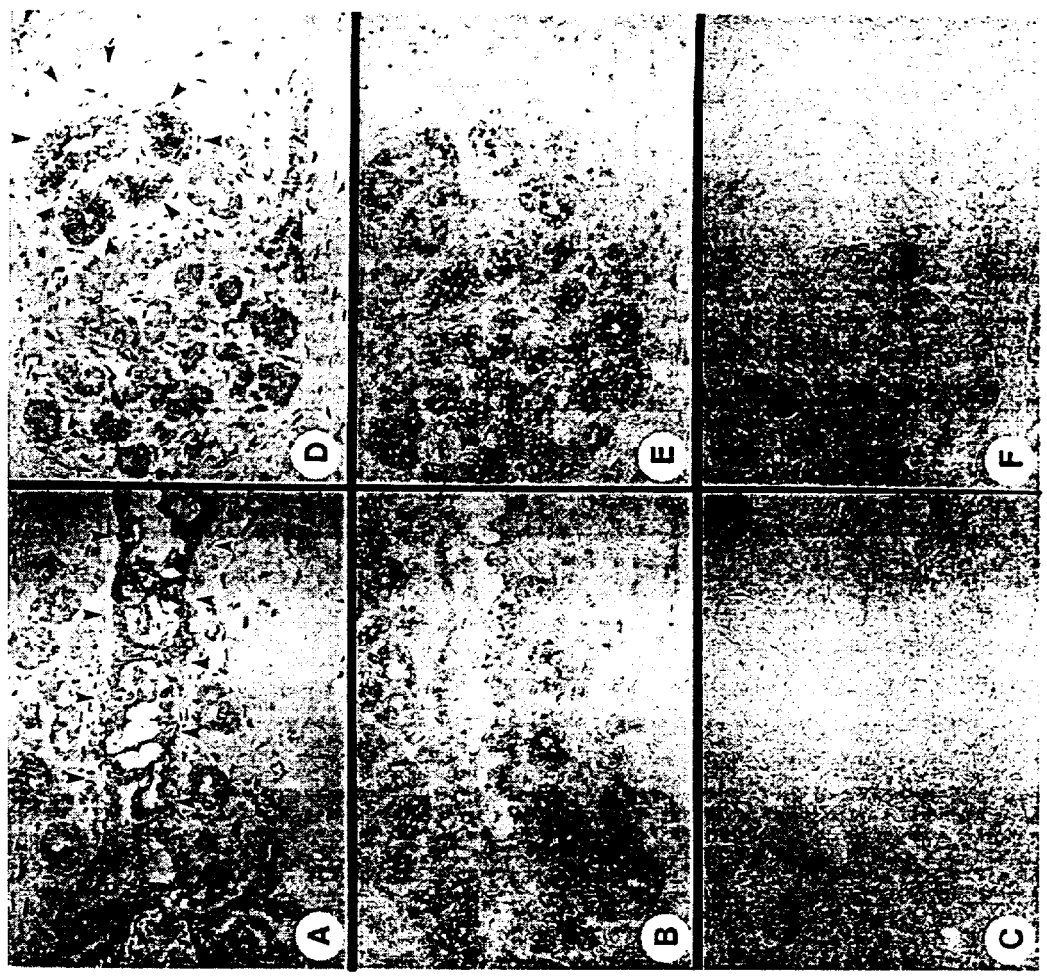
FIG. 18 shows expression of glypican-1 in human breast cancer tissue. A: Immunostaining revealed strong glypican-1 immunoreactivity in the intraductal carcinomas. D: In the lobular part, faint glypican-1 immunoreactivity was present in these cancer cells. B, E: In situ hybridization analysis of serial sections revealed strong glypican-1 mRNA signals in the lobualr part. C, F: Hybridization with the glypican-1 sense probe did not yield any specific signals. Magnification, 200.
Figure 19:
FIG. 19 shows mild hyperplasia of usual type with heaped-up cells which have "snout" like luminal aspect of cells. Note at upper right an artifact of histological sectioning which produced apparent filling of a portion of the space. Immunostaining revealed only faint glypican-1 immunoreactivity in these ductal cells (A), moderate glypincan-1 immunoreactivity in the fibroblast or myoepithelial cells surrounding the lumen (A inset). In situ hybridization analysis of serial sections revealed strong glypican-1 mRNA signals in the ductal cells (B). Hybridization with the sense glypican-1 prove did not yield any specific signals (C). Magnification 200.

Immunohistochemical analysis with the same highly specific anti-glypican-1 antibody used above revealed that the breast cancer cells exhibiting a distored morphology with prominent nuclei and abundant cytoplasm also exhibited strong glypican-1 immunoreactivity (FIGS. 18A, D, outlined by arrowhead). In contrast, the small cancer cells that had a more differentiated lobular architecture exhibited faint glypican-1 immunoreactivity (FIGS. 18A, D). Glypican-1 immunoreactivity was also present in the fibroblasts surrounding the cancer cells. In regions exhibiting intraductal epithelial hyperplasia, the proliferating epithelial cells were devoid glypican-1 immunoreactivity (FIG. 19A). In contrast, the fibroblasts and myoepithelial cells immediately adjacent to the proliferative ductal cells exhibited moderate glypican-1 immunoreactivity (FIG. 19A inset). In the normal breast tissue, glypican-1 immunoreactivity was not present in the connective tissue cells or in the terminal ductal-lobular unit.

Figure 29:
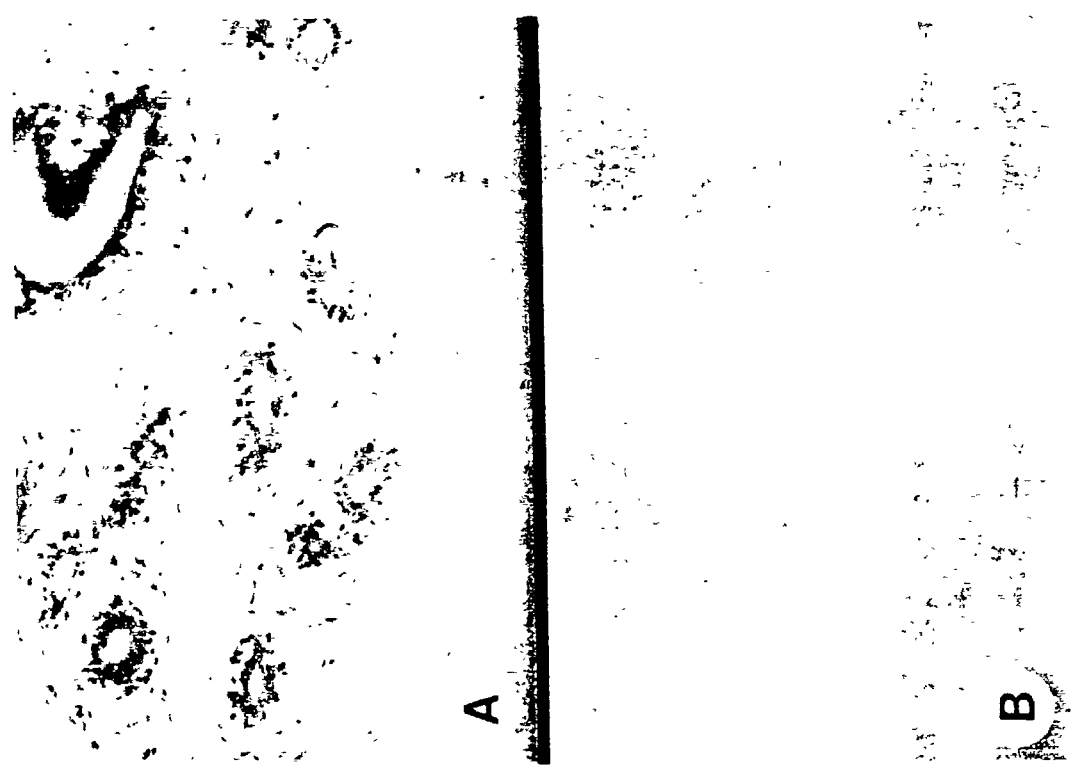
FIG. 29 shows glypican-1 expression in the normal breast tissue.

Immunohistochemical analysis of 5 normal tissues using the same highly specific anti-glypican-1 antibody did not reveal any glypican-1 immunoreactivity (FIG. 29A). In contrast, 5 of 5 cancer tissues exhibited moderate to strong glypican-1 immunoreactivity in the intraductal carcinoma cells. This immunoreactivity was most marked in cancer cells that had a distorted morphology with prominent nuclei and abundant cytoplasm (FIG. 30A, outlined by arrowheads). In contrast, the small cancer cells that had a more differentiated lobular architecture exhibited faint glypican-1 immunoreactivity (FIG. 30A). Moderate to strong glypican-1 immunoreactivity was also present in the fibroblasts surrounding the cancer cells.

In situ hybridization analysis using a highly specific riboprobe was next carried out to delineate the sites of expression of glypican-1. This analysis revealed low levels of glypican-1 mRNA in the intraductal carcinoma cells (FIG. 18B). In the lesion exhibiting a lobular architecture, there was a moderate to strong glypican-1 mRNA in situ hybridization signal (FIG. 18E). The surrounding fibroblasts exhibited a faint glypican-1 mRNA in situ hybridization. In contrast, strong glypican-1 mRNA in situ hybridization signal was found in the proliferative ducts associated with intraductal epithelial hyperplasia (FIG. 19B). A glypican-1 sense probe did not reveal any specific signal (FIGS., 18C, F, 19C).

Figure 4:
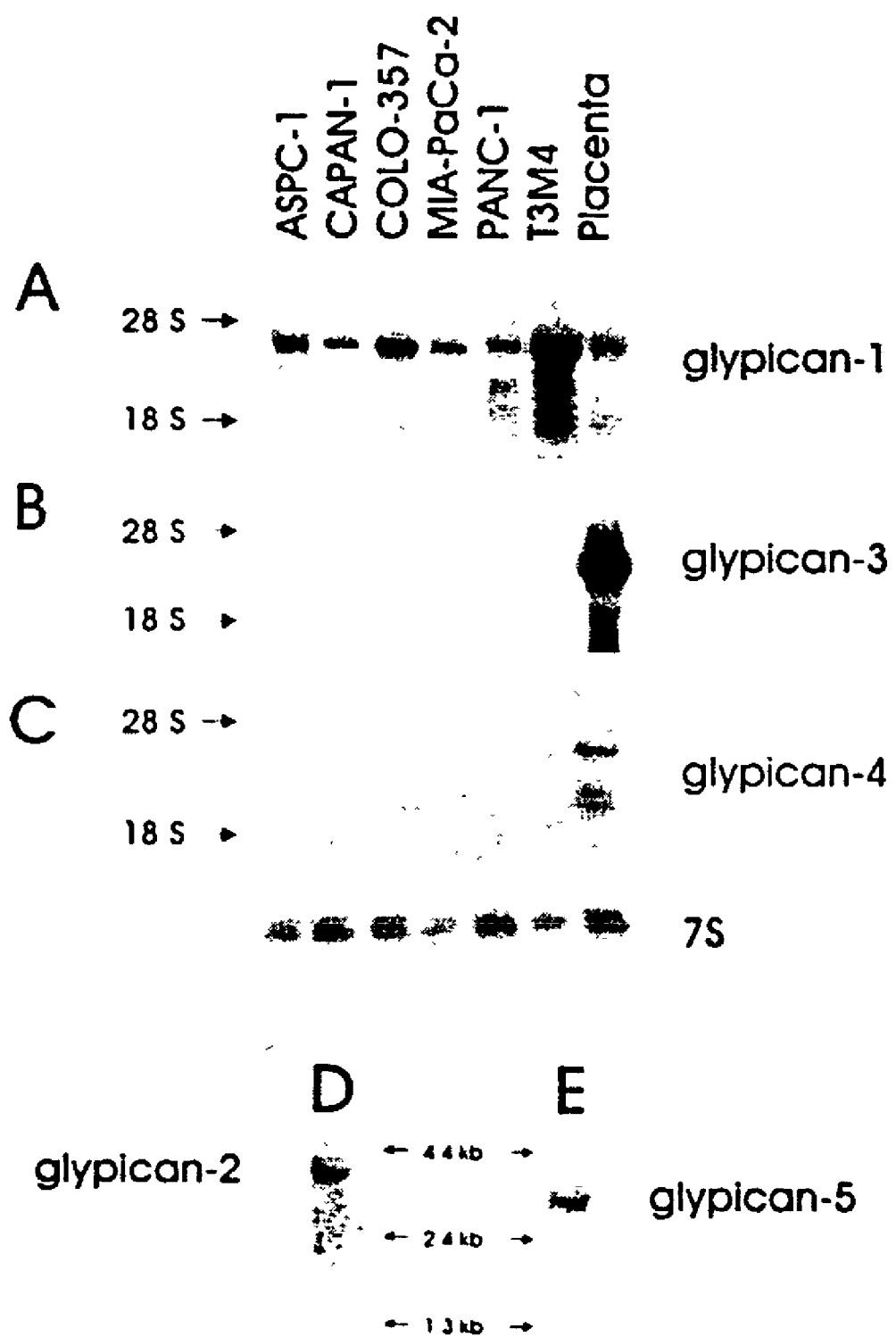
FIG. 4 shows expression of glypicans in cultured human pancreatic cancer cells and human placenta. Northern blots of total RNA (20 µg/lane) isolated from the indicated cell lines and placenta (A–C) or polyA$^+$ RNA (2 µg/lane) isolated from fetal (D) and adult (E) brain tissue were hybridized with $^{32}$P-labeled glypican-1,-2,-3,-4,-5 cDNA probes (500,000 cpm/ml) and with a 7S cDNA probe (50,000 cpm/ml). A: expression of glypican-1; B: expression of glypican-3; C: expression of glypican-4; D: positive control for glypican-2 (human fetal brain tissue); E: positive control for glypican-5 (human adult brain tissue). The 28S and 18S rRNA marker (A–C) and RNA size markers (D, E) are indicated by arrows.

Expression of Members of the Glypican Family in Human Cancer Cell Lines and Tissues To determine whether cultured pancreatic cancer cells express multiple glypicans, total RNA was isolated from six pancreatic cancer cell lines. Northern blot analysis revealed high levels of glypican-1 mRNA in T3M4 and COLO-357 cells, moderate to high levels in ASPC-1 cells, and moderate to low levels in human placenta and in CAPAN-1, MIA-PaCa-2, and PANC-1 pancreatic cancer cells (FIG. 4A). In contrast, the glypican-4 mRNA transcripts were barely detectable in the cancer cell lines, whereas glypican-2, -3, and -5 were below level of detection by Northern blot analysis in all the cancer cell lines (FIGS. 4B, C, and data not shown). Glypican-3 and -4 were expressed at moderate to high levels in human placenta (FIGS. 4B, C), whereas glypican-2, and -5 were also below level of detection in placenta RNA (data not shown). In view of the absence of glypican-2/5 signals in both the pancreatic cancer cell lines and in human placenta, hybridization of human multiple tissue Northern blots was carried out with the glypican-2/5 specific probes. As expected the glypican-2 transcript (approximately 4.0 kb, FIG. 4D) was evident in human fetal brain tissue (7) and the glypican-5 transcript (approximately 3.7 kb, FIG. 4E) was readily apparent in human adult brain tissue.

Figure 5:
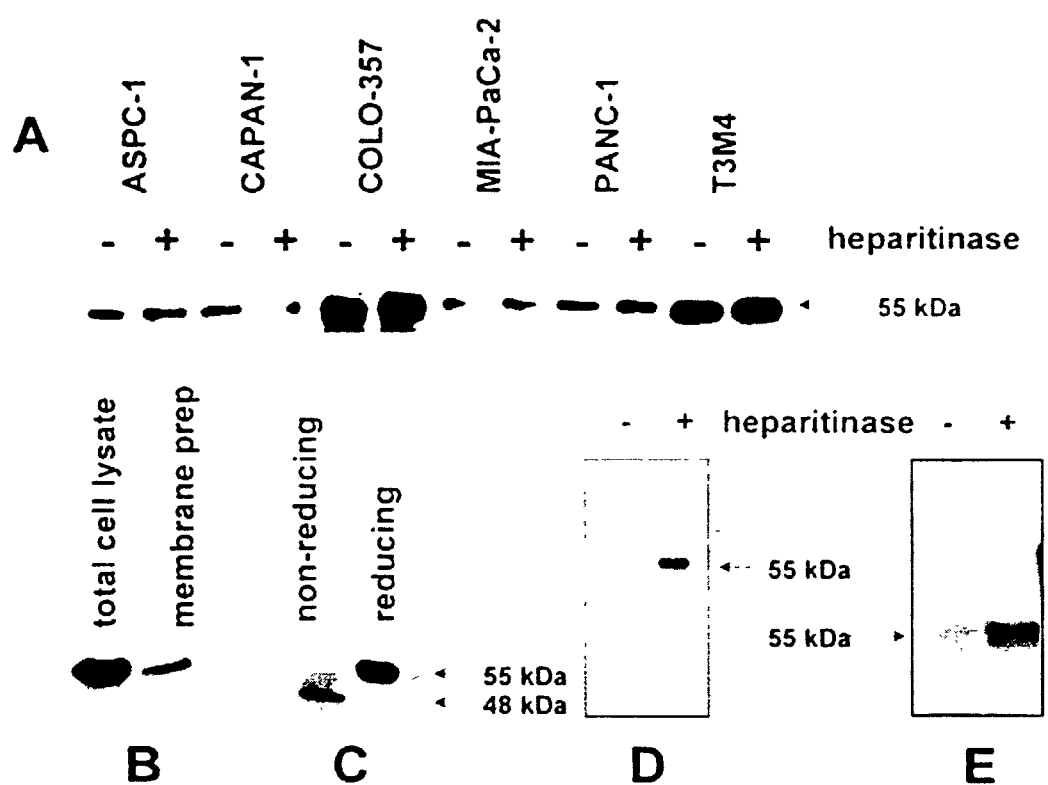
FIG. 5 shows glypican-1 protein expression in pancreatic cancer cell lines. A: 30 µg of total cell lysates prepared from the indicated cell lines were incubated in the absence (−) or presence (+) of heparitinase. B: 30 μg of total cell lysates and 30 μg of membrane proteins prepared from PANC-1 cells were digested with heparitinase. C: 30 μg of total cell lysates prepared from PANC-1 cells were subjected to heparitinase digestion and analyzed by SDS-PAGE under non-reducing and reducing conditions as described in the Methods section. D: 2.5 mg of total cell lysates prepared from PANC-1 cells were subjected to anion exchange chromatography and incubated in the absence (−) or presence (+) of heparitinase. E: PANC-1 cells were incubated for 48 h in serum-free medium. The conditioned serum-free medium (100 ml) was subjected to anion exchange chromatography and the eluted fractions were incubated in the presence (+) or absence (−) of heparitinase. Immunoblot analysis was carried out with an affinity purified rabbit anti-rat glypican-1 antibody (250 ng/ml) that also recognizes human glypican-1 (A–E).

Immunoblotting with the anti-glypican-1 antibody revealed a 55 kDa band in all 6 cell lines. In general agreement with the Northern blot data, the highest levels of glypican-1 protein were observed in COLO-357 and T3M4 cells (FIG. 5A). Because heparitinase treatment was not required for demonstrating the 55 kDa protein, we next sought to confirm its identity as glypican-1 by examining the characteristics of this protein in PANC-1 cells. First, membrane preparations (30 μg) and total cell lysates (30 μg) from PANC-1 cells were digested with heparitinase and subjected to SDS-PAGE followed by immunoblotting. The 55 kDa band was observed in the total protein lysate sample as well as in the membrane preparation sample (FIG. 5B). Second, total cell lysates (30 μg) from PANC-1 cells were subjected to heparitinase digestion and analyzed by SDS-PAGE under reducing and non-reducing conditions. The 55 kDa band that was observed under reducing conditions migrated as a band of approximately 48 kDa under non-reducing conditions (FIG. 5C). This degree of shift is characteristic of the core proteins of the glypican family, which have many disulfide bonds and migrate more rapidly under non-reducing conditions then under reducing conditions (55). Third, we isolated intact HSPGs from total cell lysates (2.5 mg) of PANC-1 cells, using anion exchange chromatography (31). When this material was digested with heparitinase, immunoblotting revealed the presence of the 55 kDa band, whereas in the absence of heparitinase this band was not detectable (FIG. 5D). These results confirm that at least part of the total glypican-1 in PANC-1 cells bears heparan sulfate and is therefore glycanated.

To determine whether glypican-1 is released into the culture medium by pancreatic cancer cells, conditioned serum-free medium from PANC-1 and COLO-357 cells was collected during a 48 h incubation, and subjected to anion exchange chromatography to isolate HSPGs. The eluted fractions were incubated in the presence or absence of heparitinase. Immunoblot analysis revealed the presence of the 55 kDa band, representing the glypican-1 core protein, in the heparitinase digested sample of PANC-1 (FIG. 5E) and COLO-357 cells (data not shown), indicating that both cells release glycanated glypican-1 into the culture medium.

Figure 20:
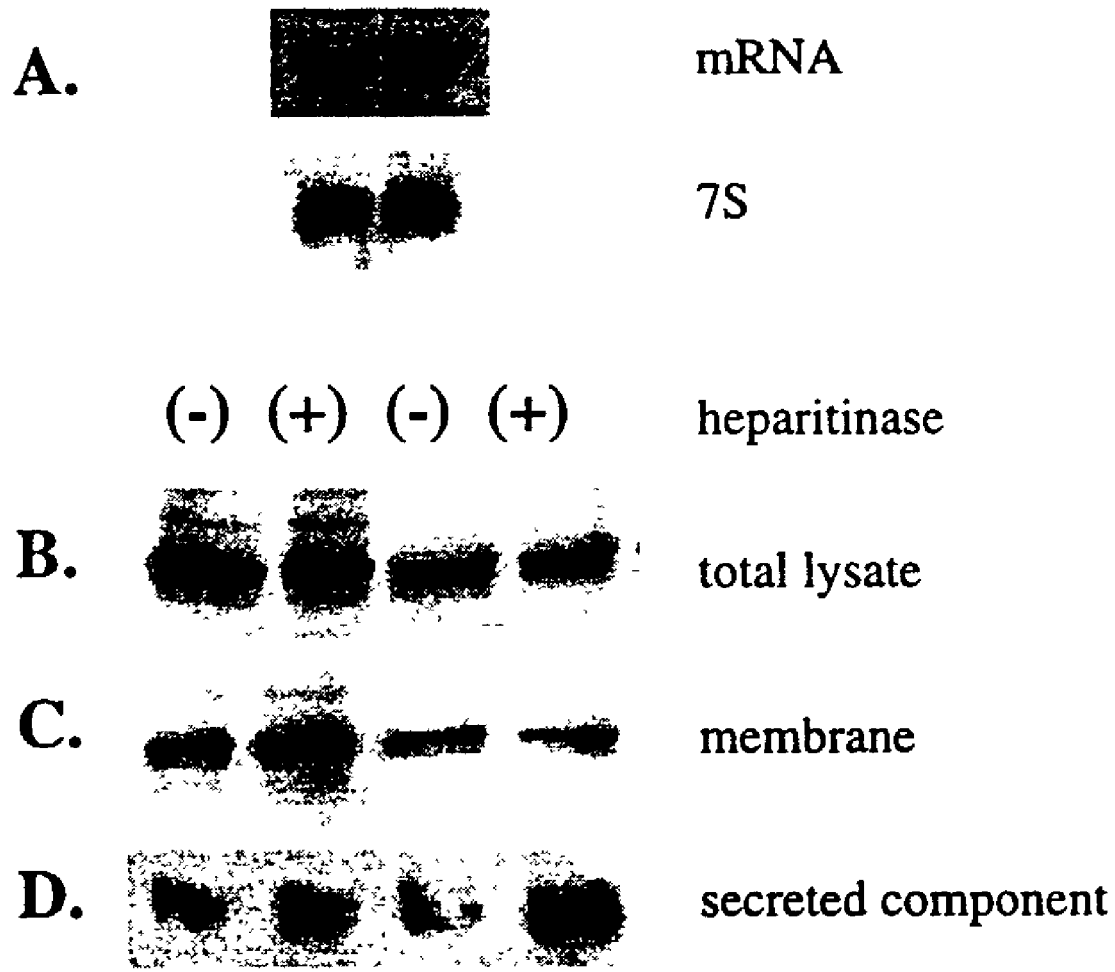
FIG. 20 shows glypican-1 expression in breast cancer cell lines. A: Northern blots of total RNA (20 μg/lane) isolated from MDA-MB-231 and MDA-MB-468 cells were hybridized with $^{32}$P-labeled glypican-1 cDNA probe (500000 cpm/ml) and with a 7S cDNA probe (50000 cpm/ml). Exposure times were 1 day for glypican-1 and 6 hours for 7S. 30 μg of total lysates (B) and 30 μg of membrane proteins (C) prepared from MDA-MB-231 and MDA-MB-468 cells were incubated in the absence (−) or presence (+) of heparitinase. D: MDA-MB-231 and MDA-MB-468 cells were incubated for 48 hours in serum-free medium. The conditioned serum-free medium (100 ml) were subjected to anion exchange chromatography and the eluted fractions were incubated in the absence (−) and presence (+) of heparitinase. Immunoblot analysis was carried out with an affinity purified rabbit anti-rat glypican-1 antibody (250 ng/ml) that also recognizes human glypican-1 (B-D).

To determine whether cultured breast cancer cells express any glypicans, total RNA was isolated from two breast cancer cell lines. Northern blot analysis revealed high levels of glypican-1 mRNA in both cell lines (MDA-MB-231 and MDA-MB-468) (FIG. 20A). In contrast, glypican-2, -3, -4 and -5 were below the level of detection by Northern blot analysis in both cell lines. Immunoblotting with a highly specific anti-glypican-1 antibody revealed the presence of a 55-kDa band corresponding to glypican-1 in total lysates from both cell lines (FIG. 20B). Heparitinase treatment was not required for demonstrating the 55-kDa protein. To assess whether there was a membrane-bound component, membrane preparations (30 μg) were digested with heparitinase and subjected to SDS-PAGE followed by immunoblotting. The 55-kDa band was also observed in the membrane samples (FIG. 20C). To determine whether glypican-1 is released by breast cancer cells, conditioned serum free medium from MDA-MB-231 and MDA-MB-468 cells was collected during a 48-h incubation, and subjected to anion exchange chromatography to isolate HSPGs. Immunoblotting revealed the presence of the 55-kDa band, representing the glypican-1 core protein (FIG. 20D). As expected, the signal was more intense in heparitinase-digested samples of both cells, indicating that both cells release glycanated glypican-1 into the culture medium.

Figure 21:
FIG. 21 shows 30 μg of total cell lysates prepared from MDA-MB-231 and MDA-MB-468 cells were subjected to heparitinase digestion and analyzed by SDS-PAGE under nonreducing and reducing conditions as described in Methods.
Figure 21:

To further confirm the identity of the 55 kDa protein as glypican-1, membrane samples (30 μg) were subjected to heparitinase digestion and analyzed by SDS-PAGE under reducing and nonreducing conditions. The 55-kDa band that was observed under reducing conditions migrated as a band of 48 kDa under nonreducing conditions (FIG. 21). This shift is characteristic of the core proteins of glypicans, since these proteins have many disulfide bonds and migrate more rapidly under nonreducing conditions than under reducing conditions (55).

Syndecan-1 Expression in Human Breast Cancer Cell Lines

Figure 22:
FIG. 22 shows syndecan-1 expression in breast cancer cell lines. A: Northern blots of total RNA (20 μg/lane) isolated from MDA-MB-231 and MDA-MB-468 cells were hybridized with $^{32}$P-labeled syndecan-1 cDNA probe (500000 cpm/ml) and with a 7S cDNA probe (50000 cpm/ml). Exposure times were 1 day for syndecan-1 and 6 hours for 7S. B: 30 μg of total lysates were prepared from MDA-MB-231 and MDA-MB-468 cells. C: MDA-MB-231 and MDA-MB-468 cells were incubated for 48 hours in serum-free medium. The conditioned serum-free medium (100 ml) were subjected to anion exchange chromatography. Immunoblot analysis was carried out with human anti-mouse syndecan-1 antibody.
Figure 22:
Figure 22:

Next we determined whether cultured breast cancer cells express syndecan-1. Northern blot analysis revealed high levels of syndecan-1 mRNA in both cell lines (MDA-MB-231 and MDA-MB-468) (FIG. 22A). Immunoblotting with a highly specific anti-syndecan-1 antibody revealed the presence of a 200-kDa band corresponding to syndecan-1 in total lysates from both cell lines (FIG. 22B). To determine whether syndecan-1 is released by breast cancer cells, conditioned serum free medium from MDA-MB-231 and MDA-MB-468 cells was collected during a 48-h incubation, and subjected to anion exchange chromatography to isolate HSPGs. Immunoblotting revealed the presence of the 200-kDa band, representing the syndecan-1 core protein (FIG. 22C), indicating that both cell lines release syndecan-1 into the culture medium.

Effects of Cleavage of GPI Anchors on Growth Factor Action

We next sought to determine whether glypican-1 regulates growth factor action in two pancreatic cancer cell lines. COLO-357 and PANC-1 cells were incubated in the presence or absence of phosphoinositide-specific phospholipase-C (PI-PLC), which cleaves glypican-1 and other proteins that associate with membranes via a covalent GPI lipid linkage. In both COLO-357 (FIG. 6A) and PANC-1 (FIG. 6B) cells, FGF2 and HB-EGF exerted a dose-dependent increase in cell proliferation. Preincubation of either cell line with PI-PLC (0.5 U/ml) and subsequent incubation with the same concentrations of FGF2 or HB-EGF in the presence of PI-PLC (0.1 U/ml) completely blocked the stimulatory effect of these heparin-binding growth factors (FIGS. 6A,B).

Figure 6:
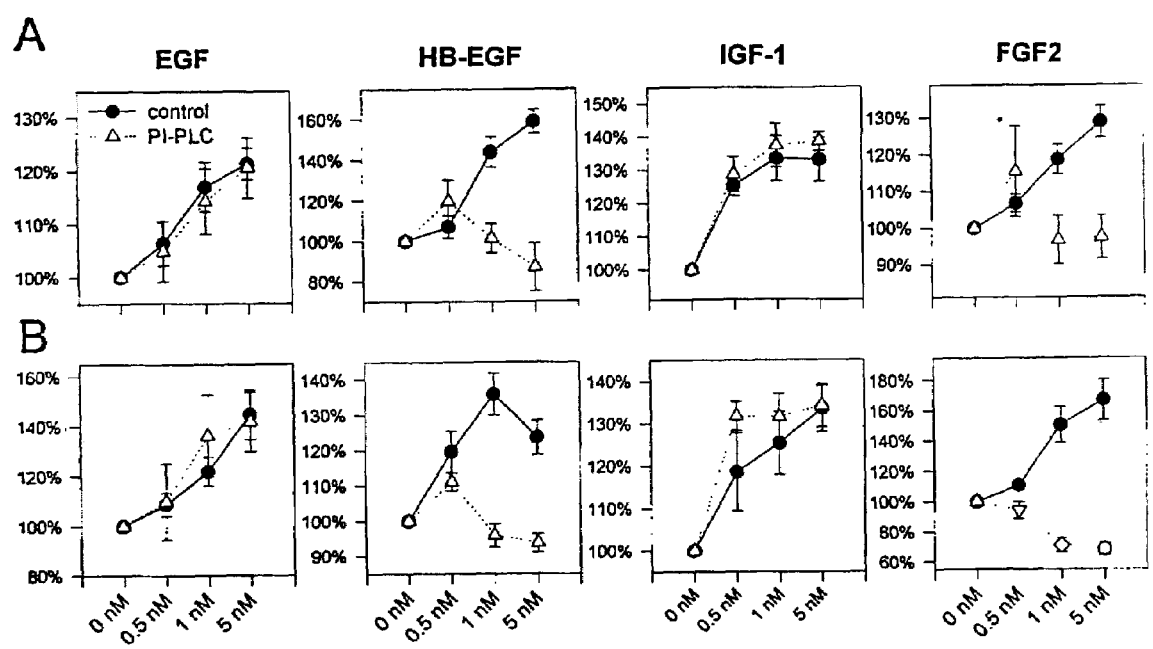
FIG. 6 shows the effects of cleavage of GPI anchors on growth factor action in pancreatic cancer cells. PANC-1 (A) and COLO-357 (B) cells were incubated with the indicated concentrations of EGF, HB-EGF, IGF-1, and FGF2 in the absence (●) or presence (ρ) of PI-PLC as described in the Methods section. Data are expressed as percent increase or decrease of the respective untreated controls and are means ±SEM of 8 determinations/experiment from three separate experiments.

In contrast, in both cell lines PI-PLC had no significant effect on the growth stimulatory actions of EGF and IGF-1, which are non-heparin binding growth factors (FIGS. 6A,B).

Figure 8:
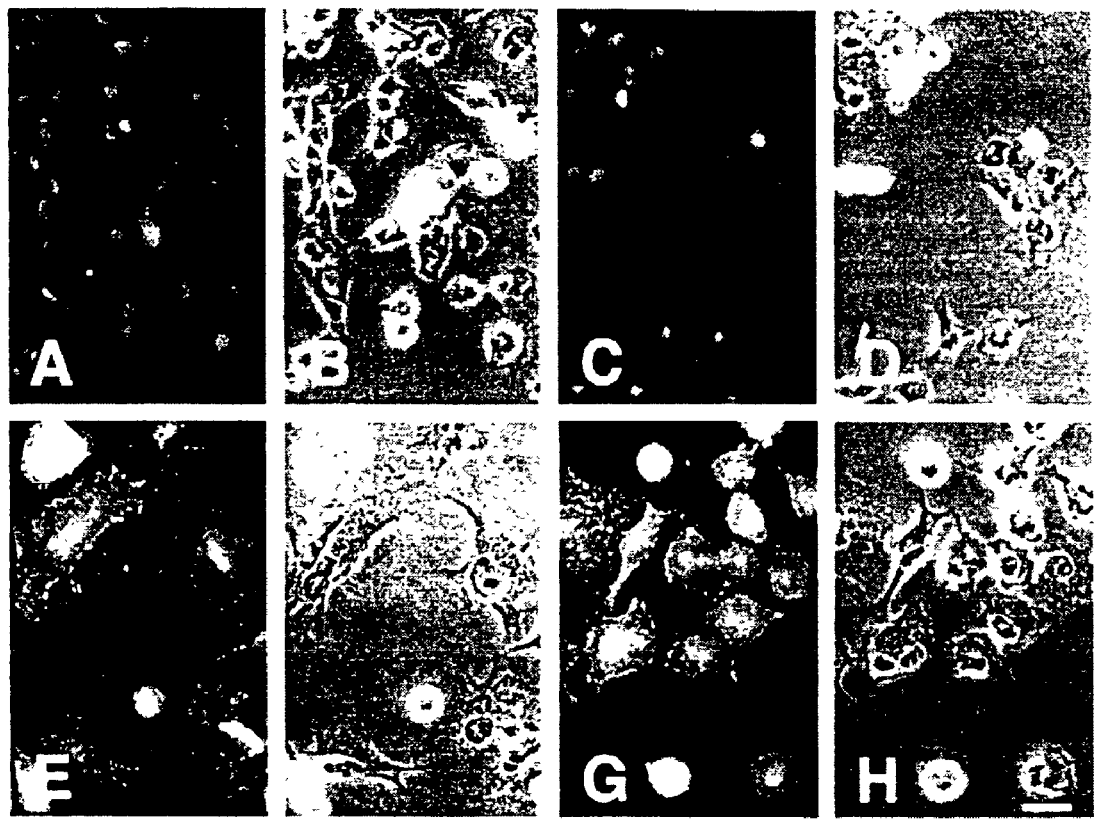
FIG. 8 shows effects of PI-PLC treatment on glypican-1 immunofluorescence in cultured cells. Sham transfected (A–D) and glyp1-VSVGTMR transfected PANC-1 cells (E-H) were incubated for 1 h in the absence (A,B,E,F) or presence (C,D,G,H) of PI-PLC (0.5 U/ml), and stained with an affinity purified rabbit anti-rat glypican-1 antibody followed by addition of Cy3-conjugated anti-rabbit antibody. Immunofluorescence (A,C,E,G) and the corresponding phase-contrast images (B,D,F,H) are shown. Scale bar: 30 μm.

In addition to removing glypicanil, PI-PLC removes other GPI-anchored proteins from the cell membrane. Therefore, we next sought to determine whether restoring glypican-1 expression could block the loss of responsiveness to heparin-binding growth factors that occurs following PI-PLC treatment. To this end, PANC-1 cells were stable transfected with a glypican-1 construct that encodes the extracellular domain of glypican-1 fused to the transmembrane domain of the vesicular stomatitis virus G glycoprotein (VSVG), and which is therefore resistant to the actions of PI-PLC. This construct was also tagged at its C-terminus with a c-myc epitope. Clones transfected with the pCDNA3.1/glyp1-VSVGTMR construct exhibited a 2.5 kb transcript by Northern blot analysis (FIG. 7A). Expression of the fusion protein was confirmed by immunoblotting with an anti-c-myc antibody (FIG. 7B). In addition, immunofluorescence was carried out in untreated control and pCDNA3.1/glyp1-VSVGTMR transfected PANC-1 cells and in the respective cells following PI-PLC treatment. Relatively low intensity signals corresponding to endogenous glypican-1 were present in parental PANC-1 cells, and these signals were further decreased by PI-PLC treatment (FIGS. 8A–D). In contrast, glypl-VSVGTMR transfected PANC-1 cells exhibited strong glypican-1 immunofluorescence signals, which were not attenuated by PI-PLC treatment (FIGS. 8E-G).

Figure 9:
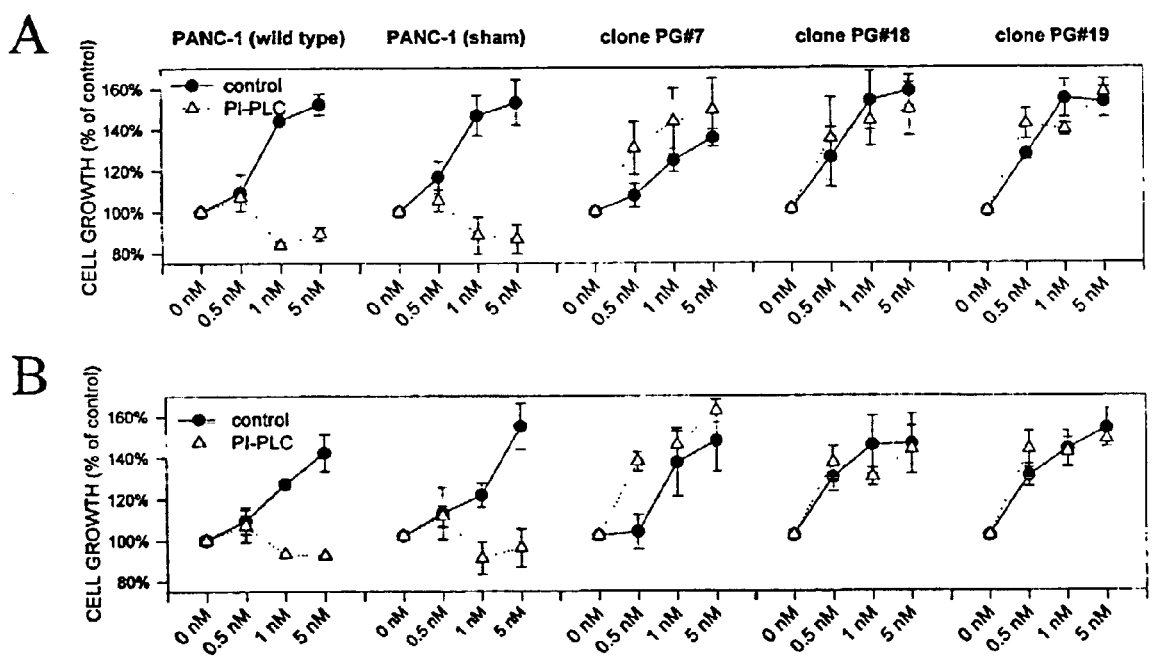
FIG. 9 shows effects of glyp1-VSVGTMR on PI-PLC mediated inhibition of heparin-binding growth factor action. Wild-type PANC-1 cells, sham-transfected PANC-1 cells, and three pCDNA3.1/glyp1-VSVGTMR transfected PANC-1 clones were incubated with the indicated concentrations of HB-EGF (A), and FGF2 (B) in the absence (●) or presence (Δ) of PI-PLC as described in the Methods section. Data are expressed as percent increase or decrease of unstimulated controls and are means ±SEM of 8 determinations/experiment from three separate experiments.

Parental PANC-1 cells, PANC-1 cells transfected with the empty vector alone (control) and three clones expressing the glyp1-VSVGTMR construct were next incubated with growth factors in the presence or absence of PI-PLC. In both parental and control PANC-1 cells, FGF2 and HB-EGF enhanced proliferation in a dose-dependent manner, and this effect was completely blocked by PI-PLC treatment (FIG. 9). In contrast, in the three glypl-VSVGTMR expressing clones, PI-PLC did not significantly alter the growth stimulatory actions of FGF2 and HB-EGF (FIG. 9). Since the glyp1-VSVGTMR construct prevented PI-PLC from blocking heparin-binding growth factor responsiveness, the effects of PI-PLC in parental PANC-1 cells were most likely due to its ability to cleave endogenous glypican-1.

Figure 23:
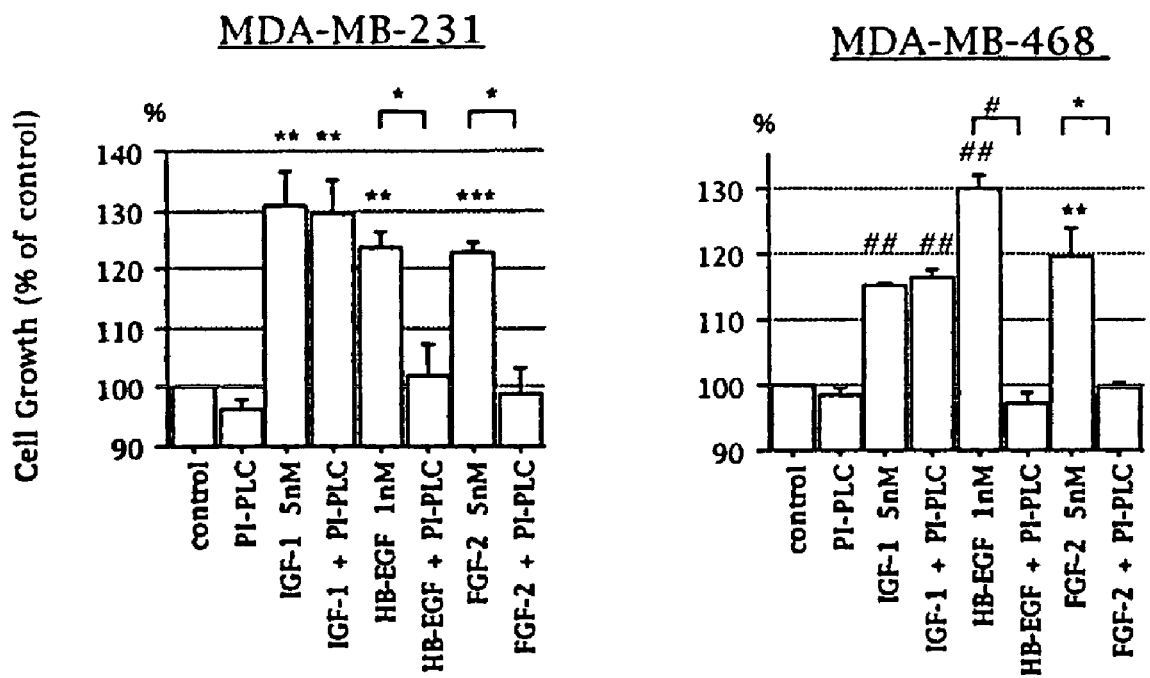
FIG. 23 shows the effects of cleavage of GPI anchors on growth factor action in breast cancer cells. MDA-MB-231 and MDA-MB-468 cells were incubated with the indicated concentrations of IGF-1, HB-EGF and FGF-2 in the absence or presence of PI-PLC as described in Methods. Data are expressed as percent increase or decrease of the respective untreated controls and are meansSEM of eight determinations per experiment from three separate experiments (#:$p<0.001$, *:$p<0.05$). :$p<0.05$, *:$p<0.01$ and ##:$p<0.005$ compared with control.

To determine whether glypican-1 regulates growth factor action in breast cancer cells. MDA-MB-231 and MDA-MB-468 cells were incubated in the absence or presence of PI-PLC. In both cell lines (FIG. 23), IGF-1, HB-EGF and FGF-2 induced cell proliferation. Preincubation of either cell line with PI-PLC (0.5 U/ml) and subsequent incubation with the same concentrations of each growth factor in the presence of PI-PLC (0.1 U/ml) completely blocked the stimulatory effect of HB-EGF and FGF-2. In contrast, in both cell lines PI-PLC had no significant effect on the growth stimulatory actions of IGF-1, which is not a heparin-binding growth factor (FIG. 23).

Effects of Reduced Glypican-1 Protein Levels on Growth Factor Responsiveness

Figure 10:
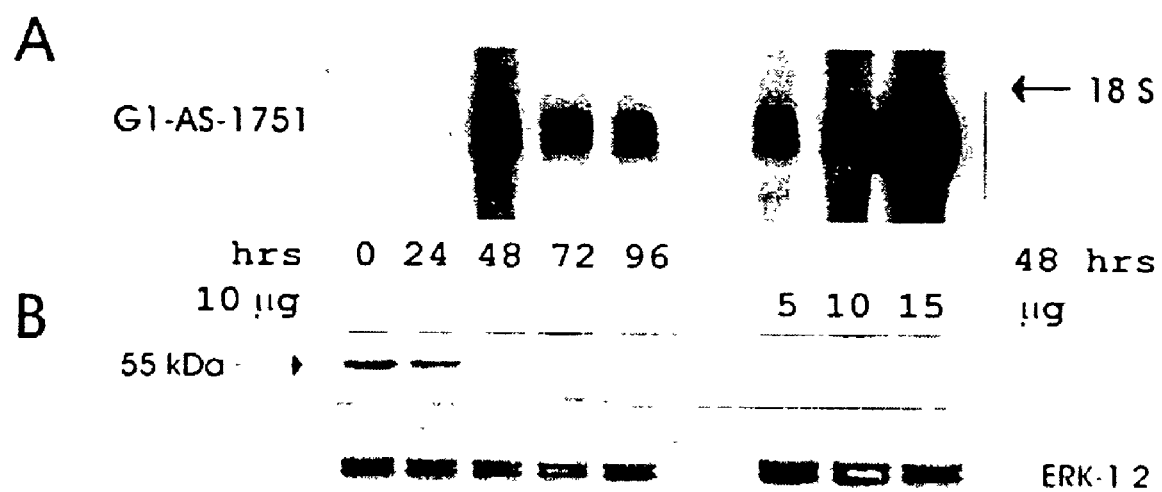
FIG. 10 shows expression of glypican-1 antisense (G1-AS-1751) mRNA and glypican-1 protein in PANC-1 cells. Total RNA (20 μg/lane) and total cell lysates (30 μg/lane) were isolated from PANC-1 cells at the indicated times after transfection with the indicated amounts of pMH6/G1-AS-1751 plasmid DNA (the total amount of transfected DNA was equal in all samples). A: Northern blots were hybridized with a $^{32}$P-labeled glypican-1 sense riboprobe (500,000 cpm/ml). Exposure time was 6 h. Equal loading was determined by ethidium bromide staining. B: Immunoblot analysis was carried using the affinity purified rabbit anti-rat glypican-1 antibody (250 ng/ml) that also recognizes human glypican-1. To confirm equal loading, the membrane was stripped and re-probed with an anti-ERK-1 antibody that cross-reacts with ERK-2. The position of ERK-1 (p44) and ERK-2 (p42) are indicated on the right.
Figure 11:
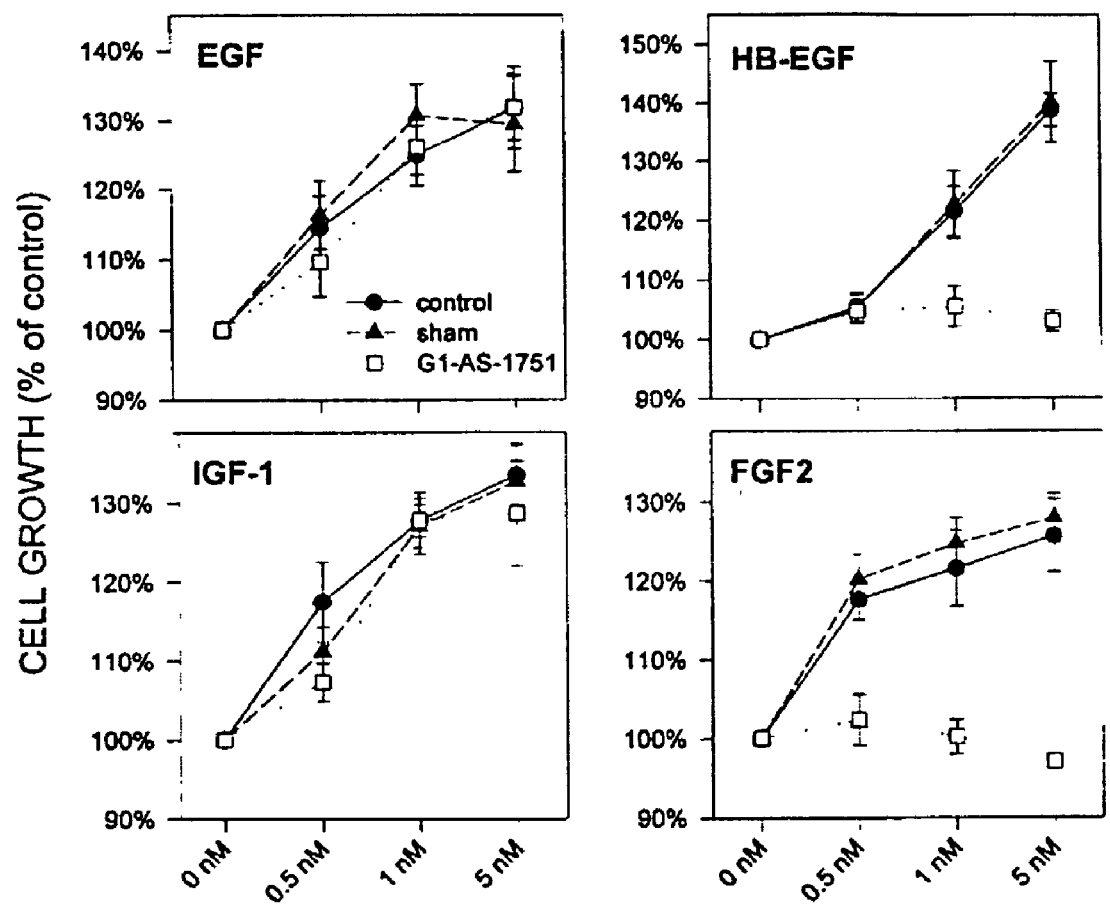
FIG. 11 shows effects of G1-AS-1751 on growth factor action in PANC-1 cells. PANC-1 cells (●), PANC-1 cells transfected with equivalent amounts of pMH6 DNA (▲), and G1-AS-1751 transfected PANC-1 cells (□) were incubated for 48 h with the indicated concentrations of EGF, HB-EGF, IGF-1, and FGF2. Data are expressed as percent change from unstimulated controls and are means ±SEM of 8 determinations/experiment from three separate experiments.

To determine whether it is possible to modulate responsiveness to heparin-binding growth factors by altering endogenous glypican-1 protein levels, we next transiently transfected PANC-1 cells with a glypican-1 antisense construct (G1-AS-1751). Following transient transfection, there was a time and dose dependent appearance of glypican-1 antisense mRNA, as determined by Northern blot analysis with a specific glypican-1 sense riboprobe (FIG. 10A). Following transfection with 10 μg plasmid DNA/4×10$^6$ cells, expression of the glypican-1 antisense mRNA was evident within 24 h. Peak expression occurred after 48 h, and was sustained for at least 96 h, (FIG: 10A). Immunoblot analysis with the highly specific glypican-1 antibody indicated that there was a parallel decrease in glypican-1 protein levels (FIG. 10B). A slight decrease was evident after 24 h, whereas maximal reduction of glypican-1 protein levels occurred at 48–96 h (FIG. 10B). Next, the effects of growth factors on cell growth were determined during the 48–96 h interval after transfection, when glypican-1 protein levels were maximally reduced. The growth stimulatory actions of EGF and IGF-1 were not significantly different from control, sham transfected, and G1-AS-1751 transfected PANC-1 cells (FIG. 11). In contrast, the growth stimulatory effects of FGF2 and HB-EGF were completely blocked in the G1-AS-1751 transfected PANC-1 cells (FIG. 11), whereas both growth factors enhanced cell proliferation in a dose-dependent manner in control and sham transfected PANC-1 cells (FIG. 11).

Figure 24:
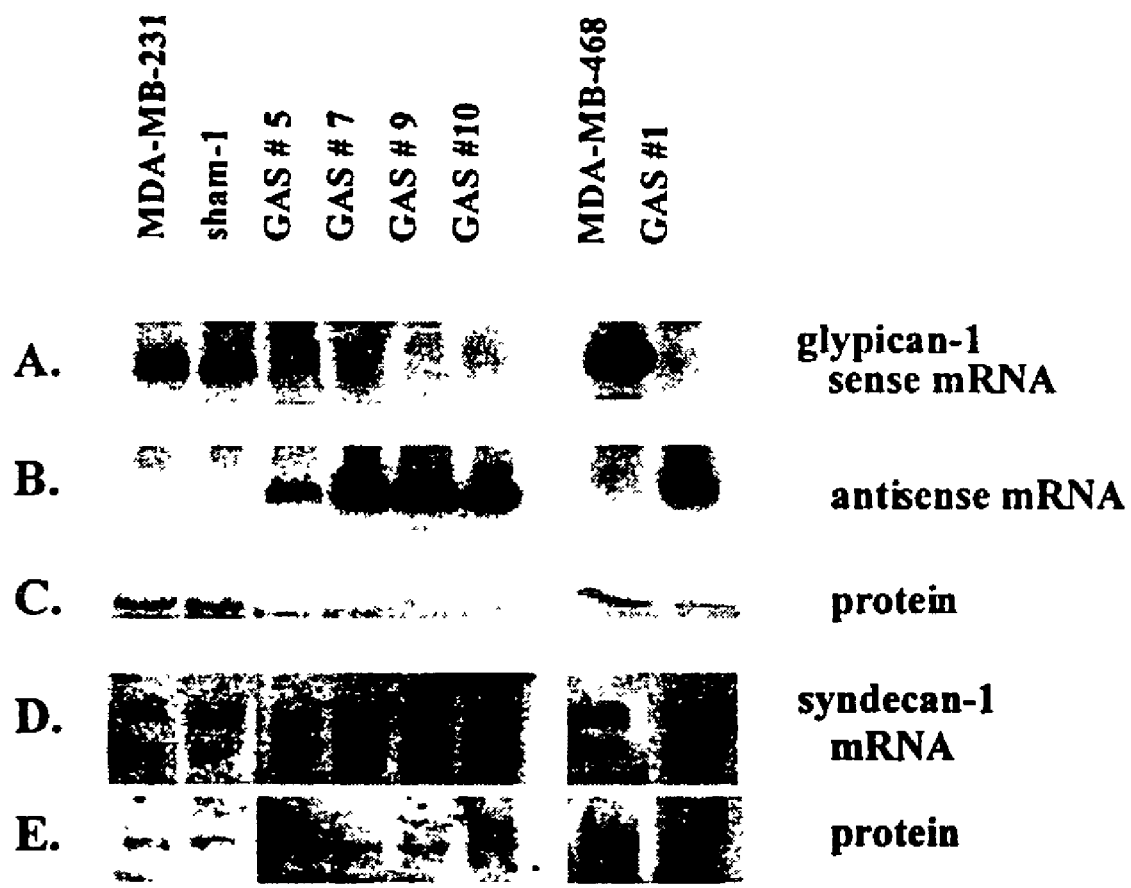
FIG. 24 shows expression of glypican-1 mRNA in the indicated MDA-MB-231 and MDA-MB-468 clones. Northern blots of total RNA (20 μg/lane) isolated from the indicated cell lines were hybridized with a $^{32}$P-labeled glypican-1 antisense riboprobe (A), and with a glypican-1 sense riboprobe (B). Equal loading was verified by ethidium bromide staining of the gel. C: 30 μg of total cell lysates of parental and glypican-1 antisense transfected MDA-MB-231 and MDA-MB-468 cells were subjected to immunoblot analysis with an affinity purified rabbit anti-rat glypican-1 antibody (250 ng/ml) that also recognizes human glypican-1. Expression of syndecan-1 mRNA (D) and protein (E) in the indicated MDA-MB-231 and MDA-MB-468 clones.
Figure 25:
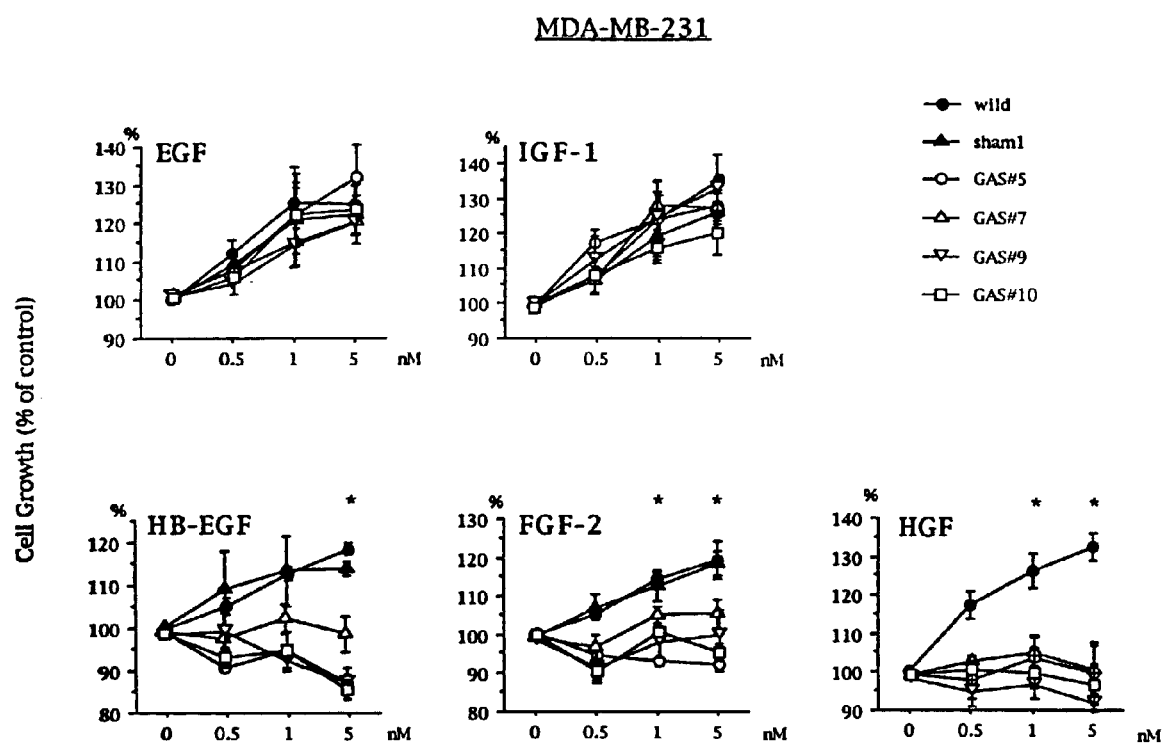
FIG. 25 shows the effects of decreased endogenous glypican-1 levels on growth factor responsiveness in MDA-MB-231 cells. Parental (●), sham transfected (▲), and 4 glypican-1 antisense (GAS) mRNA expressing MDA-MB-231 clones (open symbols) were incubated for 48 hours with the indicated concentrations of EGF, IGF-1, HB-EGF, FGF-2 and HGF. Data are expressed as percent change from unstimulated controls and are means SEM of 8 determinations per experiment from three separate experiments (*:$p<0.05$).
Figure 26:
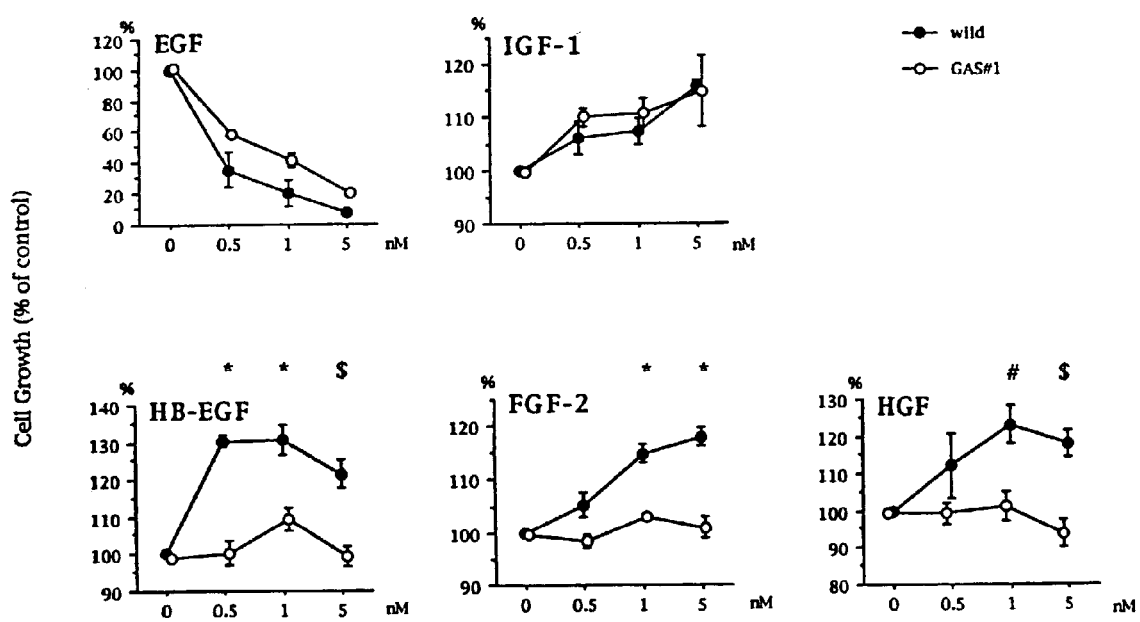
FIG. 26 shows the effects of decreased endogenous glypican-1 levels on growth factor responsiveness in MDA-MB-468 cells. Parental (●) and 1 glypican-1 antisense (GAS) mRNA expressing MDA-MB-468 clone (○) were incubated for 48 hours with the indicated concentrations of EGF, IGF-1, HB-EGF, FGF-2 and HGF. Data are expressed as percent change from unstimulated controls and are means SEM of 8 determinations per experiment from three separate experiments ($:$p<0.005$, #:$p<0.01$, *:$p<0.05$).

Since PI-PLC can remove many GPI-anchored proteins from the cell surface, we next sought to determine whether it is possible to modulate responsiveness to heparin-binding growth factors by altering endogenous glypican-1 protein levels. Accordingly, we transfected MDA-MB-231 and MDA-MB-468 cells with a glypican-1 antisense construct (G1-AS-1751). Northern blot analysis of total RNA using a glypican-1 sense riboprobe revealed high levels of glypican-1 antisense mRNA in MDA-MB-231 and MDA-MB-468 clones, whereas the parental cells and sham-transfected MDA-MB-231 cells did not exhibit a glypican-1 antisense mRNA transcript (FIG. 24A). Analysis with the antisense probe revealed that glypican-1 mRNA was expressed in parental and sham-transfected cells, but was present at very low levels in the antisense-transfected clones (FIG. 24B). There was also a marked decrease in the 55 kDa glypican-1 protein in these clones, as determined by immunoblotting (FIG. 24C). On the other hand, the transfection of glypican-1 antisense did not change the level of syndecan-1 on Northern blot and immunoblot analysis (FIGS. 24D, E). This decreased expression of glypican-1 was associated with a marked attenuation of the growth stimulatory effects of HB-EGF, FGF2 and HGF in both cell lines (FIGS. 25, 261). In contrast, the growth stimulatory actions of EGF and IGF-1 were silimar in parental, sham-transfected and glypican-1 antisense transfected cells (bc FIGS. 10, 11).

Effects of Decreased Glypican-1 Expression in PANC-1 Pancreatic Cancer Cells by Permanent Antisense Expression Ten independent PANC-1 clones were selected after 4 weeks of growth in selection medium. Northern blot analysis of total RNA with a glypican-1 sense riboprobe revealed high levels of glypican-1 antisense mRNA in 8 of 10 clones, whereas parental PANC-1 cells did not exhibit glypican-1 antisense mRNA expression. Subsequent experiments were carried out with 4 positive clones.

Figure 12:
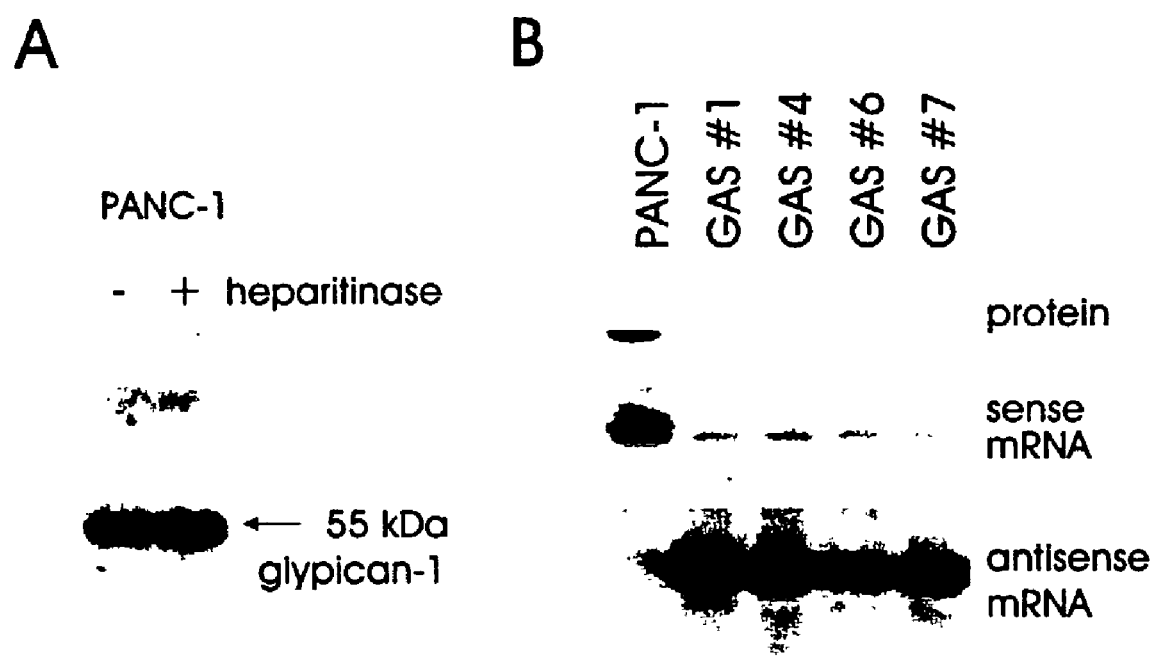
FIG. 12 shows: A: Glypican-1 protein expression in PANC-1 pancreatic cancer cells. 30 μg of total cell lysates were incubated in the absence (−) or presence (+) of heparitinase. Immunoblot analysis was carried out with an affinity purified rabbit anti-rat glypican-1 antibody (250 ng/ml) that also recognizes human glypican-1. Visualization was performed by enhanced chemiluminescence (ECL). B: Upper panel: 30 μg of total cell lysates of parental and glypican-1 antisense transfected PANC-1 cells were subjected to immunoblot analysis with an affinity purified rabbit anti-rat glypican-1 antibody (250 ng/ml). Middle and lower panel: Expression of glypican-1 mRNA in the indicated PANC-1 clones. Northern blots of total RNA (20 μg/lane) isolated from the indicated cell lines were hybridized with a $^{32}$P-labeled glypican-1 antisense riboprobe (middle panel), and with a glypican-1 sense riboprobe (lower panel). Equal loading was verified by ethidium bromide staining of the gel.

Glypican-1 generally appears on immunoblots as a faint high-molecular-weight smear, due to the high heparan-sulfate content and subsequent poor binding to blotting membranes (38, 64, and 87). After digestion with heparitinase, HSPGs including glypican-1 migrate as distinct bands. Therefore, PANC-1 cell lysates were incubated in the absence or presence of heparitinase for 6 h at 37° C. and subjected to SDS-PAGE. A 55 kDa band corresponding to the glypican-1 core protein was visible in the absence or presence of heparitinase treatment (FIG. 12A). Above we have confirmed the identity of this 55 kDa protein as glypican-1, and we have also shown that heparitinase treatment is not required for demonstrating glypican-1 expression in pancreatic cancer cells. Immunoblot analysis of parental and glypican-1 antisense transfected PANC-1 cells revealed the 55 kDa glypican-1 protein in PANC-1 cells and a very faint band corresponding to the 55 kDa glypican-1 protein in the glypican-1 antisense transfected PANC-1 clones that was only faintly visible after prolonged exposure of the immunoblot (FIG. 12B). Furthermore, Northern blot analysis with a glypican-1 antisense probe demonstrated markedly decreased glypican-1 mRNA levels in the antisense transfected cells in comparison to the parental cells (FIG. 12B).

Figure 13:
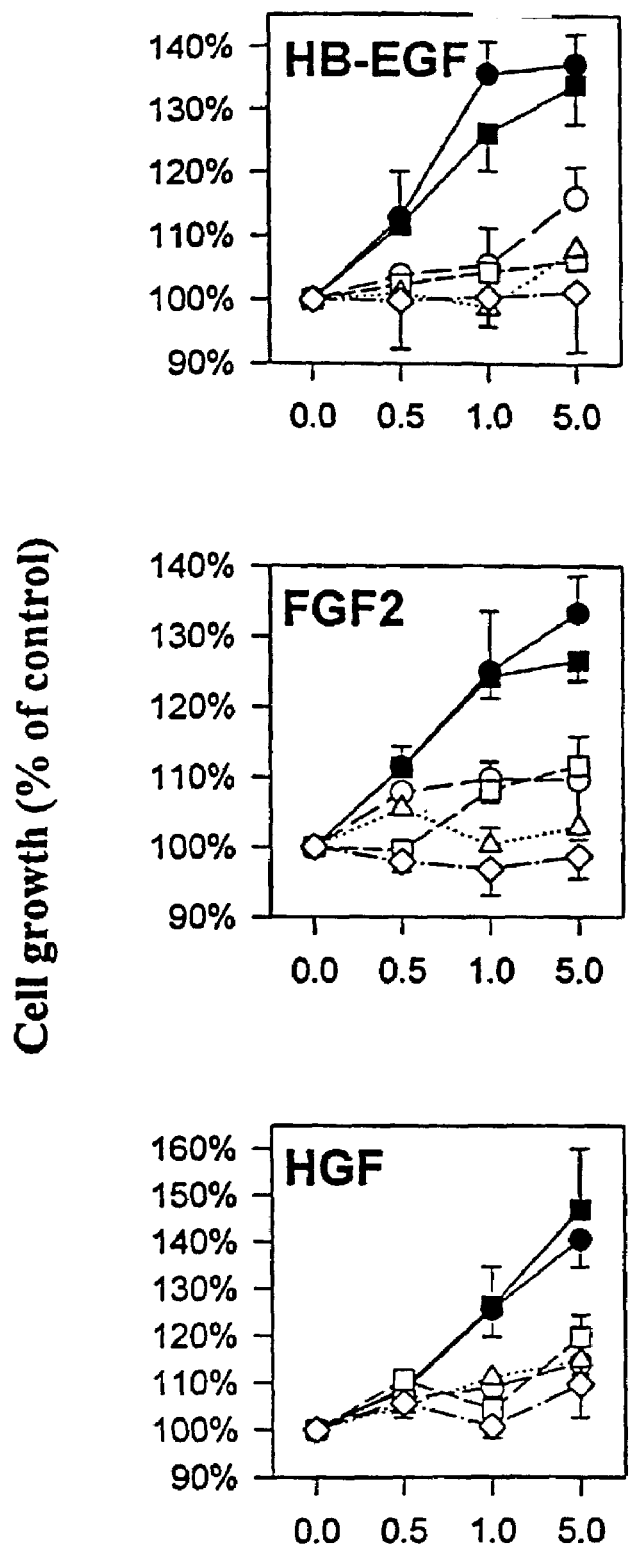
FIG. 13 shows the effects of decreased endogenous glypican-1 levels on heparin-binding growth factor responsiveness in PANC-1 cells. Parental (●), sham transfected (■), and 4 glypican-1 antisense mRNA expressing PANC-1 clones (open symbols) were incubated for 48 h with the indicated concentrations of HB-EGF, FGF2, and HGF (in nM). Data are expressed as percent change from unstimulated controls and are means ±SEM of 8 determinations per experiment from three separate experiments.
Figure 14:
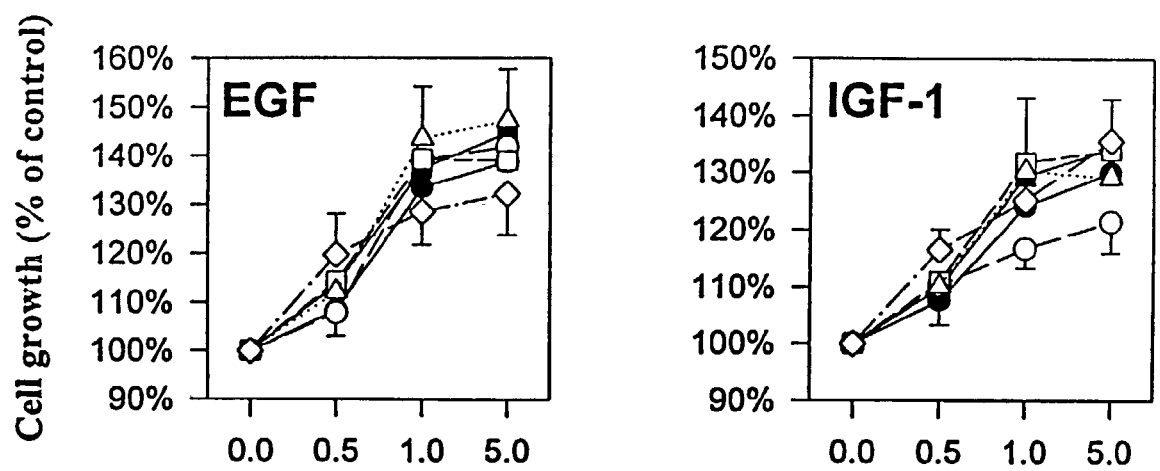
FIG. 14 shows the effects of decreased endogenous glypican-1 levels on non-heparin-binding growth factor responsiveness in PANC-1 cells. Parental (●), sham transfected (■), and 4 glypican-1 antisense mRNA expressing PANC-1 clones (open symbols) were incubated for 48 h with the indicated concentrations of EGF and IGF-1 (in nM). Data are expressed as percent change from unstimulated controls and are means ±SEM of 8 determinations per experiment from three separate experiments.

To determine whether the prolonged decrease in endogenous glypican-1 expression altered growth factor responsiveness, the effects of 3 heparin binding growth factors (HB-EGF, FGF2, and HGF) and 2 non-heparin binding growth factors (EGF and IGF-1) on cell growth were determined. FGF2, HB-EGF, and HGF enhanced proliferation in a dose-dependent manner in parental and sham transfected PANC-1 cells, and this stimulatory effect was markedly attenuated in the glypican-1 antisense transfected PANC-1 clones (FIG. 13). In contrast, the growth stimulatory actions of EGF and IGF-1 were similar in parental, sham transfected, and glypican-1 antisense transfected PANC-1 cells (FIG. 14).

Figure 15:
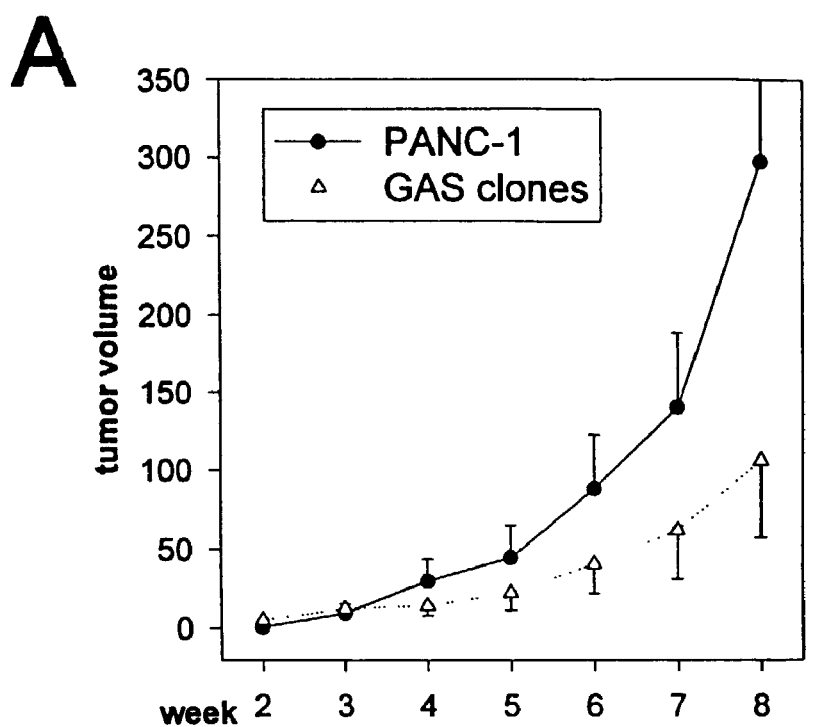
FIG. 15 shows the effects of decreased endogenous glypican-1 levels on in vivo tumorigenicity in PANC-1 cells. Exponentially growing parental, sham, and glypican-1 antisense transfected PANC-1 cells ($1 \times 10^6$) were injected subcutaneously in athymic nude mice and tumor growth was measured weekly until week 8. A: Tumor volume was determined by the equation: vol=(l×h×w)×π/4, where l is length, h is height, and w is width of the tumor. Measurements of 12 tumors for parental and sham transfected PANC-1 cells and of 24 tumors for the 4 glypican-1 antisense PANC-1 clones were combined and graphed as means ±SEM (in mm$^3$). One representative mouse for the control group (top) and another for the transfected group (bottom) after 8 weeks of tumor growth are shown in B. Scale bar 20 mm.
Figure 15:
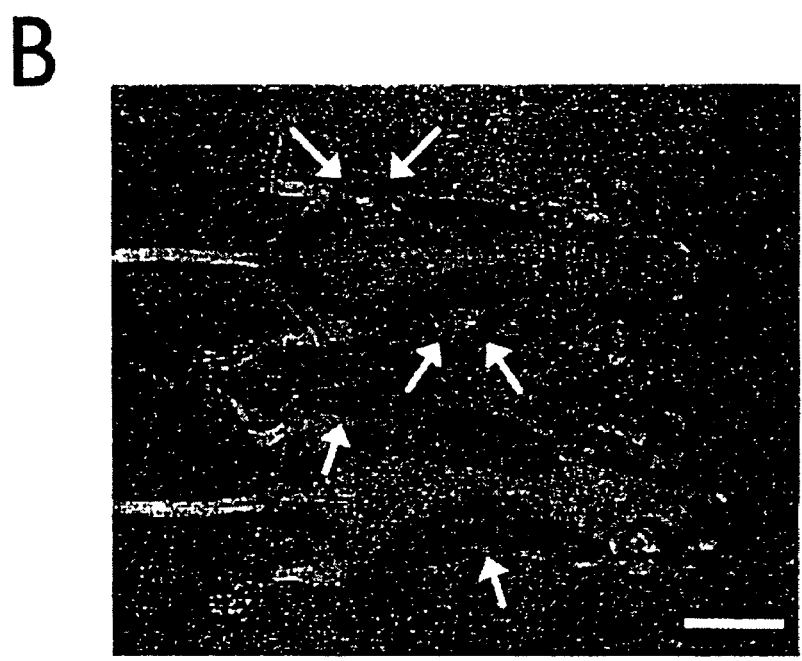
Figure 16:
FIG. 16 shows expression of glypicans and syndecan-1 in breast tissues. Total RNA (20 μg/lane) from four normal breast tissues (N) and eight breast cancers (Ca) were subjected to Northern blot analysis using a $^{32}$P-labeled glypican-1 (A), -3 (B), -4 (C) and syndecan-1 (D) cDNA probes (500000 cpm/ml). A 7S ribosomal cDNA probe (50000 cpm/ml) was used as a loading and transfer control. Exposure times were 1 day for glypican-1, -3 and syndecan-1, 2 days for glypican-4 and 6 hours for 7S. Arrows indicate the two glypican-4 mRNA transcripts (3.4 and 4.6 kb).
Figure 16:
Figure 16:
Figure 16:
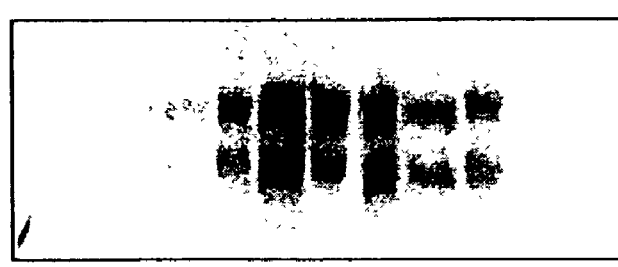
Figure 16:
Figure 17:
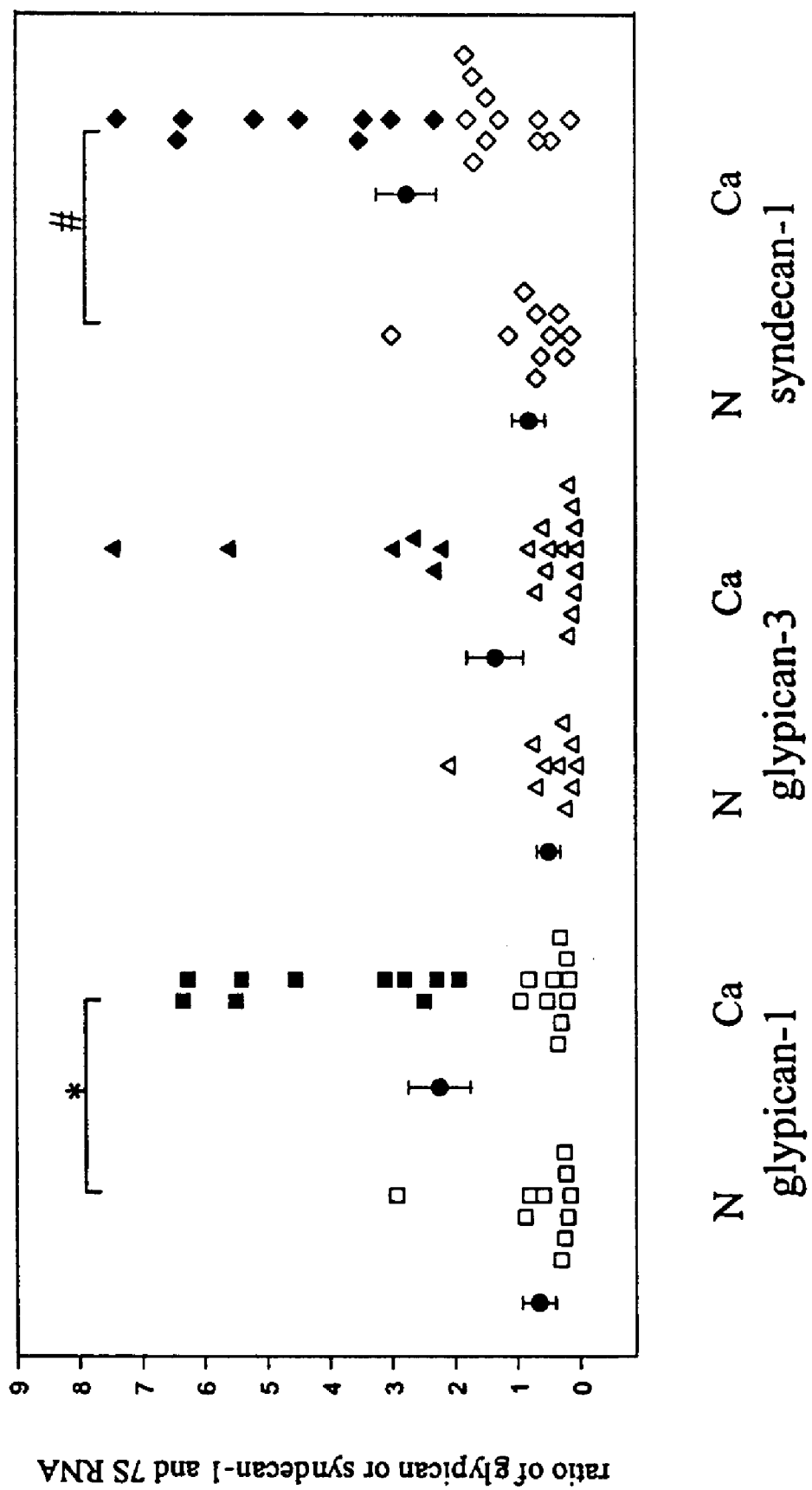
FIG. 17 shows relative expression of glypican-1, glypican-3 and syndecan-1 mRNA. Autoradiographs of Northern blots for glypican-1, glypican-3 or syndecan-1 and 7S RNA from 10 normal and 20 cancerous breast tissue samples were analyzed by densitometry and the level of glypican-1, glypican-3 or syndecan-1 expression was calculated as the ratio of glypican-1 (■), glypican-3 (▲) or syndecan-1 (◆) and 7S RNA. Closed symbols are high expressing groups of breast cancer tissues for glypican-1, glypican-3 and syndecan-1. Data are expressed as median glypican-1, -3 and syndecan-1 scores ●±SD. The median glypican-1 and syndecan-1 scores of the cancerous samples were significantly greater than the median from normal breast tissue samples (*:$p<0.05$, #:$p<0.01$).

To determine whether the decrease in endogenous glypican-1 levels and the subsequent blockage of heparin binding growth factor signaling in the glypican-1 antisense transfected PANC-1 clones resulted in enhanced tumorigenicity in vivo, cell growth in a nude mice model was examined next. To this end, $1 \times 10^6$ parental, sham transfected, or glypican-1 antisense transfected PANC-1 cells were injected subcutaneously at each site in athymic (nude) mice and tumor growth was measured weekly to compare tumorigenicity of glypican-1 antisense mRNA expressing PANC-1 cells with parental and sham transfected cells. During the first three weeks, there was no significant difference of tumor growth between the parental, sham transfected, and glypican-1 antisense transfected cells. Starting at week 4 after tumor cell injection, however, parental and sham transfected cells exhibited a more rapid tumor growth in comparison to glypican-1 antisense mRNA expressing PANC-1 clones (FIG. 15A). By 8 weeks following tumor cell injection, there was a 64% decrease in growth in the antisense expressing clones by comparison with control cells. A representative nude mouse for each group is shown in FIG. 15B.

(3) DISCUSSION

HSPGs are thought to play an important role in growth factor signaling, a role that has been particularly well documented for FGFs (88, 120, and 8). HSPGs are essential for the interactions of FGFs with their high affinity receptors in a number of cell types, including CHO cells, 3T3 fibroblasts, lymphoid cells, myeloblasts (72), chondrocytes, and MCF-7 breast cancer cells (17). HSPGs may act by increasing the affinity of FGFs for their receptors, facilitating receptor dimerization and subsequent signaling, and/or stabilizing FGFs by protecting them from proteolysis or thermal denaturation. HSPGs have also been shown to be essential for mitogenic signaling of HB-EGF in rat vascular smooth muscle cells (27) and rat gastric mucosal cells (67), and may serve as co-receptors for a variety of other secreted growth factors including vascular endothelial growth factor, hepatocyte growth factor, and members of the Wnt, TGF-β and Hedgehog families. Furthermore, HSPGs of the glypican family—glypican-3 and Drosophila Dally—have been implicated in the control of cellular growth. Mutations in Dally produce morphological defects in certain fly tissues by affecting patterned cell divisions, and glypican-3 mutations cause the Simpson-Golabi-Behmel overgrowth syndrome in man.

In breast cancer, there are several reports that HSPGs could be responsible for differences in their proliferative and invasive properties (17, 53). HSPGs are known to interact with FGF-2, KGF, VEGF, HB-EGF and HGF. HGF and FGF are known to regulate the morphogenesis and differentiation of mammary epithelial cells, and HSPGs are likely to be important regulators of the development of the gland. Moreover, HSPGs are differently distributed in normal and malignant breast epithelial cells, and this difference in HSPG distribution correlates with differences in sensitivity to FGF2. Together, these observations suggest that altered expression and function of HSPGs may contribute to the aberrant growth of breast cancer cells.

We determined that human pancreatic cancers overexpress glypican-1 at both the mRNA and protein levels. By Northern blot analysis, there was an 8-fold increase in glypican-1 mRNA levels in the cancer tissues. None of the cancer samples exhibited an abnormal-sized glypican-1 transcript. Western blot analysis revealed the anticipated 55 kDa core protein in 4 of 6 cancer samples but in none of the tested normal samples. The 55 kDa glypican-1 core protein was evident only following heparitinase treatment, which is in agreement with the observation in other tissues that intact glypican-1 migrates as a broad high-molecular-weight smear on SDS-PAGE. These findings indicate that the majority of glypican-1 in pancreatic cancer tissues is glycosylated with heparan sulfate.

Human breast cancers also overexpress several glypicans and syndecan-1 at the mRNA level. By Northern blot analysis, there was a significant 6.4 fold increase in glypican-1 mRNA levels in the cancer tissues by comparison with the normal controls. There was also a slight increase in glypican-3 and -4 mRNA levels in the cancer samples. The overall increase in glypican-3 mRNA levels in the cancer samples almost achieved statistical significance. Furthermore, a subgroup of the breast cancer samples exhibited a significant increase in glypican-3 mRNA levels by comparison with the mean level in the normal samples. Glypican-2 and -5 mRNA transcripts were below the level of detection in either the normal or the cancer samples. In syndecan-1 mRNA levels, there was a significant 2.8 fold increase in the cancer tissues by comparison with the normal controls. Together, these observations suggest that glypican-1, -3, -4 and syndecan-1 may have a role in breast cancer biology, but that glypican-1 is the principal glypican that is overexpressed in breast cancer.

By immunohistochemistry, strong glypican-1 immunoreactivity was present in a heterogeneous pattern in the cancer cells forming intraductal and lobular carcinomas, and in the fibroblasts surrounding the cancer cells but not in the fibroblasts that were more distant from the tumor. A moderate to strong glypican-1 mRNA in situ hybridization signal was also present in the cancer cells, and, to a lesser extent, in the fibroblasts immediately adjacent to the cancer cells. These observations suggest that breast cancer cells produce and release glypican-1, and that some of the glypican-1 present in the fibroblasts surrounding the breast cancer cells in vivo derives from the cancer cells. In support of this hypothesis, both breast cancer cell lines examined in the present study were formed to express and secrete glypican-1. MDA-MB-231 and MDA-MB-468 breast cancer cell lines expressed glypican-1 on the cell surface, as determined by immunoblotting of solubilized membrane preparations. The presence of glypican-1 on the cell surface suggested that it may enhance the interaction of heparin binding growth factors with their high affinity receptors. Indeed, treatment of cells with PI-PLC, an enzyme that removes surface bound glypicans by cleaving GPI-anchored proteins, abrogated the mitogenic effects of HB-EGF and FGF-2 in both cell lines. These observations suggest that the mitogenic effects of these growth factors are dependent on the presence of surface bound glypican-1. However, PI-PLC might also remove other GPI-anchored proteins from the cell surface. Therefore, we also generated clones of stably transfected MDA-MB-231 and MDA-MB-468 cells expressing a glypican-1 antisense construct. These clones exhibited a marked decrease in endogenous glypican-1 mRNA and protein level, and a marked attenuation of the mitogenic response to several heparin-binding growth factors (HB-EGF, HRG-α, HRG-β, FGF-2 and HGF) that act through four distinct tyrosine kinase receptors (45). In contrast, IGF-1, which is not heparin-binding growth factor, exerted similar mitogenic effects in parental, sham and glypican-1 antisense transfected cells.

In contrast to the breast cancer cells, the proliferative lesions exhibiting a pattern of intraductal epithelial hyperplasia did not harbor glypican-1 immunoreactivity. However, the fibroblasts and myoepithelial cells immediately adjacent to the proliferative ductal cells exhibited moderate glypican-1 immunoreactivity. Furthermore, in situ hybridization analysis revealed that strong glypican-1 mRNA signal was found in the proliferative ducts associated with intraductal epithelial hyperplasia. It is likely, therefore, that these proliferative lesions, like the breast cancer cells produce and release glypican-1.

Only faint glypican-1 immunoreactivity was evident in the pancreatic cancer cells within the tumor mass. In contrast, the fibroblasts immediately adjacent to the cancer cells exhibited intense glypican-1 immunoreactivity. However, by in situ hybridization glypican-1 was expressed at high levels in both the cancer cells and the adjoining fibroblasts. Inasmuch as glypican-1 is known to exist on the surface of cells as both a lipid-anchored form and as a peripheral membrane proteoglycan, most likely derived by shedding, these observations suggest that some of the glypican-1 that is associated with fibroblasts surrounding pancreatic cancer cells in vivo is derived from the cancer cells. This conclusion is supported by the observation that all 6 pancreatic cancer cell lines expressed abundant amounts of glypican-1 mRNA and protein, and that glypican-1 was present in the conditioned medium of both tested cell lines, PANC-1 and COLO-357.

Immunoblotting with a glypican-1 specific antibody revealed the presence of a 55-kDa protein in the pancreatic cancer cell lines even in the absence of heparitinase digestion Nonetheless, three lines of evidence suggest that this protein is glypican-1. First, Western blotting demonstrated the presence of this protein in membrane preparations. Second, under non-reducing conditions the 55-kDa protein migrated as a band of approximately 48 kDa. This is characteristic of glypicans, which are highly disulfide-bonded and exhibit greater mobility in non-reducing gels. Third, purification of HSPGs from total cell lysates by anion exchange chromatography demonstrated that at least some glycanated (heparan sulfate-bearing) glypican-1 is made by these cells. Together, these observations suggest that some of the glypican-1 synthesized by cultured pancreatic cancer cells is not glycanated, as can occur in cells engineered to produce abnormally high levels of HSPG core proteins (unpublished observations). Alternatively, it is possible that some of the heparan sulfate chains on glypican-1 are removed post-synthetically by the cancer cells. Consistent with the latter possibility, it is known that cancer cells of many types, especially those with high metastatic potential, release high levels of heparanases, enzymes that degrade heparan sulfate.

Previous work has established that a variety of polypeptide growth factors and their receptors are overexpressed in human pancreatic cancer, including heparin binding growth factors such as FGF2 (24) and HB-EGF. These growth factors enhance the proliferation of cultured human pancreatic cancer cell lines in vitro and it has been suggested that aberrant autocrine and paracrine activation of mitogenic pathways by these growth factors may contribute to pancreatic cancer cell growth in vivo. Inasmuch as heparin-dependent growth factors can be stored in the extracellular matrix to protect them against proteolytic degradation the abundance of glypican-1 in the fibroblasts surrounding the tumor suggests that it may participate in the storage of these growth factors. As cancer cells invade this stroma, it is possible that these growth factors are released (e.g. by heparanases) for subsequent mitogenic stimulation of the cancer cells. It is conceivable, however, that glypican-1 present on fibroblasts adjacent to the tumor may also act to dampen the mitogenic response to these growth factors. For example, in keratinocytes, glypican-1 enhances the mitogenic response to FGF1, while inhibiting the mitogenic response to FGF7. Furthermore, inhibiting proteoglycan sulfation in MDA-MB-231 human breast cancer cells decreases binding of FGF2 to HSPGs and restores responsiveness to FGF2 mitogenic signals.

Three lines of evidence suggest that glypican-1 plays an important role in FGF2 and HB-EGF signaling in pancreatic carcinoma cell lines. First, treatment of COLO-357 and PANC-1 pancreatic cancer cells with PI-PLC abrogated selectively the mitogenic effects of FGF2 and HB-EGF in these cell lines, implying that a GPI-anchored molecule plays an essential role in FGF-2 and HB-EGF-(but not IGF-1- or EGF-) mediated signaling. Second, FGF2- and HB-EGF-mitogenesis were unaffected by PI-PLC in PANC-1 cells that have been engineered to express a transmembrane-anchored form of glypican-1. Since glypicans are the only known GPI-anchored HSPGs, and the expression levels of glypicans-2, -3, -4, or -5 are exceedingly low in pancreatic cancer cell lines, we conclude that endogenous glypican-1 (or another GPI-anchored molecule for which glypican-1 can substitute) is the PI-PLC-sensitive molecule that is normally required for such growth factor signaling. Third, reduction of glypican-1 protein levels in PANC-1 following expression of a glypican-1 antisense construct was associated with a marked attenuation of the mitogenic effects of FGF2 and HB-EGF in these cells, without altering EGF and IGF-1 induced mitogenesis.

The glypican-1 antisense clones also displayed a markedly attenuated capacity to grow in vivo. Thus, starting at week four after tumor cell injection, the growth rate of the antisense expressing clones was considerably slower than that of parental and sham transfected PANC-1 cells. To our knowledge, this is the first demonstration that suppression of expression of any glypican genes can result in attenuated tumorigenic potential in vivo. While the mechanisms whereby inhibition of glypican-1 synthesis leads to a marked attenuation of tumor growth in vivo are not completely understood, it is well established that pancreatic cancers overexpress a variety of heparin-binding growth factors. For example, pancreatic cancers express high levels of HB-EGF, FGF1, FGF2, FGF5, and HGF. It is likely therefore, that suppression of glypican-1 expression interferes with the in vivo mitogenic effects of these growth factors. In addition, all of these growth factors are known to be angiogenic, and it is generally accepted that in order for tumor size to exceed 1–2 mm in vivo, cancer cells must acquire a capacity to stimulate angiogenesis. Thus, it is also possible that decreased glypican-1 levels in the microenvironment around the cancer cells attenuates the angiogenic effects of these heparin-binding growth factors, thereby suppressing pancreatic growth indirectly.

HB-EGF and EGF signal by activating the same receptors, which are members of the EGF receptor family). However, only HB-EGF signaling was abrogated by PI-PLC. This observation suggests that the requirement for glypican-1 is at or upstream of the level of the receptor, precisely what one would expect for a molecule that acts by modulating or modifying growth factor-receptor interactions (i.e. a co-receptor). Apparently, non-GPI-anchored HSPGs (e.g. a syndecan) on the surface of pancreatic carcinoma cells do not support this function in the absence of glypican-1, a result that is somewhat surprising given the fact that transfected syndecans are known to be able to confer FGF2 sensitivity upon HSPG-deficient cells. It is possible therefore, that pancreatic carcinoma cells are lacking in syndecans, or alternatively, that the co-receptor functions of glypicans and syndecans are not interchangeable.

Because of the potentially widespread roles of cell surface HSPGs in growth factor signaling, it is tempting to speculate that up-regulation of HSPG expression would be common in malignancies, yet this is apparently not the case. Instead, a decrease in the expression of cell surface HSPGs, the amount of heparan sulfate, the fraction of total glycosaminoglycan present as heparan sulfate, and the extent of sulfation of heparan sulfate, has been reported in association with cancers of the bladder, prostate, and lung and with the oncogenic activation of cells in vitro. Furthermore, in squamous cell carcinomas, the level of syndecan-1 correlates inversely with tumor grade, stage and clinical outcome. It will be interesting to determine whether the up-regulation of glypican-1 in pancreatic cancer is a unique feature of this neoplasm.

The fact that glypican-1 is not up-regulated either in fibroblasts distant from the cancer cells, or in fibroblasts in chronic pancreatitis, even though this condition is associated with increased growth factor expression and the production of excessive stroma, points to an important paracrine interaction between pancreatic cancer cells and the adjacent fibroblasts. Together with the observation that glypican-1 is essential for mitogenic signaling of FGF2 and HB-EGF in pancreatic cancer cells, our findings raise the possibility that glypican-1 plays a crucial role in neoplastic transformation and tumor progression in this malignancy.

To directly assess the potential role of glypican-1 in breast cancer cell growth, we also characterized the consequences of altered glypican-1 expression in culture breast cancer cell lines (MDA-MB-231 and MDA-MB-468). Under basal conditions, both cell lines expressed glypican-1, as determined at the mRNA and protein levels. PI-PLC, an enzyme that cleaves GPI-anchored protein, abrogated selectively the mitogenic effects of HB-EGF and FGF-2 in both cell lines, suggesting that the mitogenic effects of these heparin-binding growth factors in breast cancer cells are dependent on the presence of surface bound glypican-1. Because PI-PLC might remove other GPI-anchored proteins from the cell surface, we also generated clones of stably transfected breast cancer cell lines expressing a glypican-1 antisense construct. These clones exhibited a marked decrease in endogenous glypican-1 mRNA and protein level, and marked attenuation of the mitogenic response to three heparin-binding growth factors (HB-EGF, FGF-2 and HGF). In contrast, EGF and IGF-1 (on MDA-MB-468, only IGF-1), which are not heparin-binding growth factors, exerted similar effects in parental, sham and glypican-1 antisense transfected cells.

Syndecan-1 was also expressed at high levels in some of the breast cancer samples as well as in the breast cancer cell lines. Two lines of evidence suggest that this HSPG is not as crucial as glypican-1 for the activation of mitogenic signaling by heparin-binding growth factors in breast cancer cells. First, syndecan-1 is not a GPI-anchored molecule and is therefore not removed from the cell-surface by PI-PLC treatment. Second, clones expressing the glypican-1 antisense did not exhibit a decrease in syndecan-1, yet were no longer responsive to heparin-binding growth factors. Together, these observations show that glypican-1 plays a pivotal role in enhancing the growth promoting effects of heparin-binding growth factors in breast cancer cells. Therefore, pharmacological or molecular interventions that interfere with glypican-1 function or expression are useful therapeutics in breast cancer as well as in pancreatic cancer. In addition, the ability of breast cancer cells to synthesize and secrete glypican-1 at high levels show that that glypican-1 is a useful marker for this cancer both as a serum assay and as an in vitro diagnostic (illustrated in our micrographs).

The therapeutic and diagnostic uses of glypican-1 and glypican-1 binding agents and suppressing agents are much the same in breast cancer, pancreatic cancer or any other glypican-1 responsive cancer (as demonstrated to be responsive by the tests described herein). Therapeutic reagents operate by suppressing the glypican-1 responsive cancer by either removing the extracellular domain of the glypican (e.g., cleavage with an enzyme), binding to that domain (e.g., an antibody or drug molecule) or actually preventing the expression of that domain (as in an antisense transfection). In vitro and in vivo diagnostics operate by binding to or otherwise detecting the glypican-1 molecules. In the case of in vitro diagnostics a reporter molecule is attached to a glypican-1 binding molecule and used to image original or metastatic cancers.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES

1 Arreaza, G. and D. A. Brown. 1995. Sorting and intracellular trafficking of a glycosylphosphatidylinositol-anchored protein and two hybrid transmembrane proteins with the same ectodomain in Madin-Darby canine kidney epithelial cells. J. Biol. Chem. 270:23641–7.

2 Asundi, V. K., B. F. Keister, R. C. Stahl, and D. J. Carey. 1997. Developmental and cell type-specific expression of cell surface heparan sulfate proteoglycans in the rat heart. Exp. Cell Res. 230:145–53.

3 Baldwin, R. L., and M. Korc. 1993. Growth inhibition of human pancreatic carcinoma cells by transforming growth factor beta-1. Growth factors. 8:23–34.

4 Bansal, R., Kumar, M., Murray, K., and Pfeiffer, S. E. Developmental and FGF-2-mediated regulation of syndecans (1–4) and glypican is oligodendrocytes. Mol.Cell.Neurosci., 7: 276–288, 1996.

5 Baselga, J., Norton, L., Albanell J., Kim, Y. M., and Mendelsohn, J. Recombinant humanized anti-HER2 antibody (Herceptin™) enhances the antitumor activity of paclitaxel and doxorubicin against HER2/neu overexpressing human breast cancer xenografts. Cancer Res., 58: 2825–2831, 1998.

6 Baselga, J., Tripathy, D., Mendelsohn, J., Baughman, S., Benz, C. C., Dantis, L., Skalrin, N. T., Seidman, A. D., Hudis, C. A., Moore, J., Rosen, P. P., Twaddell, T., Henderson, I. C., and Norton, L. Phase II study of weekly intravenous recombinant humanized anti-p185HER2 monoclonal antibody in patients with HER2/neu-overexpressing metastatic breast cancer. J.Clin.Oncol., 14: 737–744, 1996.

7 Bernfield, M., R. Kokenyesi, M. Kato, M. T. Hinkes, J. Spring, R. L. Gallo, and E. J. Lose. 1992. Biology of the syndecans: a family of transmembrane heparan sulfate proteoglycans. Ann. Rev. Cell Biol. 8:365–393.

8 Bonneh-Barkey, D., M. Shlissel, B. Berman, E. Shaoul, A. Admont, I. Vlodavsky, D. J. Carey, V. K. Asundi, R. Reich-Slotky, and D. Ron. 1997. Identification of glypican as a dual modulator of the biological activity of fibroblast growth factors. J. Biol. Chem. 272:12415–12421.

9 Carey, D. J. and D. M. Evans. 1989. Membrane anchoring of heparan sulfate proteoglycans by phosphatidylinositol and kinetics of synthesis of peripheral and detergent-solubilized proteoglycans in Schwann cells. J. Cell Biol. 108: 1891–1897.

10 Carey, D. J., K. Conner, V. K. Asundi, D. J. Omahony, R. C. Stahl, L. Showalter, G. Smith, J. Hartman, and L. I. Rothblum. 1997. cDNA cloning, genomic organization, and in vivo expression of rat N-syndecan. J. Biol. Chem. 272: 2873–9.

11 Chandler, L. A., Sosnowski, B. A., Greenlees, L., Aukerman, S. L., Baird, A., and Pierce, G. F. Prevalent expression of fibroblast growth factor (FGF) receptors and FGF2 in human tumor cell lines. Int.J.Cancer, 81: 451–458, 1999.

12 Chiang, M. K. and J. G. Flanagan. 1995. Interactions between the Flk-1 receptor, vascular endothelial growth factor, and cell surface proteoglycan identified with a soluble receptor reagent. Growth Factors. 12:1–10.

13 David, G. 1993. Integral membrane heparan sulfate proteoglycans. FASEB J. 7:1023–1030.

14 David, G., V. Lorie, B. Decock, P. Marynen, J. -J. Cassiman, and H. Van den Berghe. 1990. Molecular cloning of a phosphatidylinositol-anchored membrane heparan sulfate proteoglycan from human lung fibroblasts. J. Cell. Biol. 111:3165–3176.

15 De Klerk, D. P. 1984. Glycosaminoglycans of human prostatic cancer. J. Urol. 131:1008–1012.

16 De Klerk, D. P. 1985. The glycosaminoglycans of human bladder cancers of varying grade and stage. J. Urol. 134:978–981.

17 Delehedde, M., Deudon, E., Boilly, B., and Hondermarck, H. Production of sulfated proteoglycans by human breast cancer cell lines: binding to fibroblast growth factor-2. J.Cell Biochem., 64: 605–617, 1997.

18 Delhedde, M., E. Deudon, B. Boilly, and H. Hondermarck. 1996. Heparan sulfate proteoglycans play a dual role in regulating fibroblast growth factor-2 mitogenic activity in human breast cancer cells. Exp. Cell Res. 229:398–406.

19 Ebert, M., Yokoyama, M., Friess, H., Büchler, M. W., and Korc, M. Coexpression of the c-met proto-oncogene and hepatocyte growth factor in human pancreatic cancer. Cancer Res., 54:5775–5778, 1994.

20 Ebert, M., M. Yokoyama, M. S. Kobrin, H. Friess, M. E. Lopez, M. W. Büchler, G. R. Johnson, and M. Korc. 1994. Induction and expression of amphiregulin in human pancreatic cancer. Cancer Res. 54:3959–3962.

21 Ethier, S. P. Growth factor synthesis and human breast cancer progression. J.Natl.Cancer Inst., 87: 964–973, 1995.

22 Filla, M. S., P. Dam, and A. C. Rapraeger. 1998. The cell surface proteoglycan syndecan-1 mediates fibroblast growth factor-2 binding and activity. J. Cell. Physiol. 174: 310–321.

23 Filmus, J., J. G. Church, and R. N. Buick. 1988. Isolation of a cDNA corresponding to a developmentally regulated transcript in rat intestine. Mol. Cell. Biol. 8:4243–4249.

24 Folkman J. The role of angiogenesis in tumor growth. Semin Cancer Biol 1992; 3:65–71.

25 Freeman, C., and C. R. Parish. 1997. A rapid quantitative assay for the detection of mammalian heparanase activity. Biochem. J. 325:229–237.

26 Friess, H., J. Kleeff, and M. W. Büchler. 1997. Growth factors and growth factor receptors in chronic pancreatitis. In: Advances in pancreatic disease. Georg Thieme Verlag Struttgart/New York. Ed. Dervenis C G. pp 26–32.

27 Fukuda, K., Y. Inui, S. Kawata, S. Higashiyama, Y. Matsuda, Y. Maeda, T. Igura, S. Yoshida, N. Tanaguchi, and Y. Matsuzawa. 1995. Increased mitogenic response to heparin-binding epidermal growth factor-like growth factor in vascular smooth muscle cells of diabetic rats. Arterioscler. Thromb. Vasc. Biol. 15:1680–1687.

28 Gengrinovitch, S., Berman, B., David, G., Witte, L., Neufeld, G., and Ron, D. Glypican-1 is a VEGF165 binding proteoglycan that acts as an extracellular chaperone for VEGF165. J.Biol.Chem., 274: 10816–10822, 1999.

29 Greenlee, R. T., Hill-Harmon, M. B., Murray, T., and Thun, M. Cancer statistics, 2001. CA Cancer J. Clin. 2001, 51: 15–36, 2001.

30 Gold E B, Goldin S B. Epidemiology of and risk factors for pancreatic cancer. Surg Oncol Clin N Am 1998; 7:67–91.

31 Herndon M. E. and A. D. Lander. 1990. A diverse set of developmentally regulated proteoglycans is expressed in the rat central nervous system. Neuron 4:949–961.

32 Higashiyama, S., Abraham, J. A., and Klagsbrun, M. Heparin-binding EGF-like growth factor stimulation of smooth muscle cell migration: dependence on interactions with cell surface heparan sulfate. J.Cell Biol., 122: 933–940, 1993.

33 Hortobagyi, G. N. Treatment of breast cancer. N. Engl. J. Med., 339: 974–984, 1998.

34 Inki, P., H. Joensuu, R. Gronman, P. Klemi, and M. Jalkanen. 1994. Association between syndecan-1 expression and clinical outcome in squamous cell carcinoma of the head and neck. Br. J. Cancer 70:319–323.

35 Inoue, R., Fukutomi, T., Ushijima, T., Matsumoto, Y., Sugimura, T., and Nagao, M. Germline mutation of BRCA1 in Japanese breast cancer families. Cancer Res., 55: 3521–3524, 1995.

36 Inoue, R., Ushijima, T., Fukutomi, T., Fukami, A., Sugimura, H., Inoue, S., Okonogi, H., Sugimura, T., Matsumoto, Y., and Nagao, M. BRCA2 germline mutations in Japanese breast cancer families. Int.J.Cancer, 74: 199–204, 1997.

37 Itoh, K. and S. Y. Sokol. 1994. Heparan sulfate proteoglycans are required for mesoderm formation in Xenopus embryos. Development. 120:2703–11.

38 Ivins, J. K., E. D. Litwack, A. Kumbasar, C. S. Stipp, and A. D. Lander. 1997. Cerebroglycan, a developmentally regulated cell-surface heparan sulfate proteoglycan, is expressed on developing axons and growth cones. Dev. Biol. 184:320–332.

39 Jackson, R. L., Busch, S. J., and Cardin, A. D. Glycosaminoglycans: molecular properties, protein interactions, and role in physiological process. Physiol.Rev., 71: 481–539, 1991.

40 Kleeff J, Ishiwata T, Kumbasar A, Friess H, Büchler M W, Lander A D, Korc M. The cell-surface heparan sulfate proteoglycan glypican-1 regulates growth factor action in pancreatic carcinoma cells and is overexpressed in human pancreatic cancer. J Clin Invest 1998; 102:1662–1673.

41 Kloppel, G. and B. Maillet. 1991. Chronic pancreatitis: evolution of the disease. Hepatogastroenterology. 38:408–412.

42 Kobrin, M. S., H. Funatomi, H. Friess, M. W. Büchler, P. Stathis, and M. Korc. 1994. Induction and expression of heparin-binding EGF-like growth factor in human pancreatic cancer. Biochem. Biophys. Res. Commun. 202:1705–1709.

43 Kopreski, M. S., Lipton, A., Harvey, H. A., and Kumar, R. Growth inhibition of breast cancer cell lines by combinations of anti-p185HER2 monoclonal antibody and cytokines. Anticancer Res., 16: 433–436, 1996.

44 Korc, M. 1996. Growth factors in pancreatic cancer. In: Advances in pancreatic disease. Georg Thieme Verlag Stuttgart/New York. Ed. Dervenis C G. pp 34–41

45 Korc, M. Role of growth factors in pancreatic cancer. Surg. Oncol. Clin. N. Am., 7: 25–41, 1998.

46 Korc, M., B. Chandrasekar, Y. Yamanaka, H. Friess, M. W. Büchler, and H. G. Beger. 1992. Overexpression of the epidermal growth factor receptor in human pancreatic cancer is associated with concomitant increase in the levels of epidermal growth factor and transforming growth factor alpha. J. Clin. Invest. 90:1352–1360.

47 Kornmann M, Arber N, Korc M. Inhibition of basal and mitogen-stimulated pancreatic cancer cell growth by cyclin D1 antisense is associated with loss of tumorgenicity and potentiation of cytotoxicity to cisplatinum. J Clin Invest 1998; 101:344–352.

48 Kornmann, M., T. Ishiwata, H. G. Beger, and M. Korc. 1997. Fibroblast growth factor-5 stimulates mitogenic signaling and is overexpressed in human pancreatic cancer: evidence for autocrine and paracrine actions. Oncogene. 15:1417–1424.

49 Kosir, M. A., C. C. Quinn, K. L. Zukowski, D. J. Grignon, S. Ledbetter. 1997. Human prostate carcinoma cells produce extracellular heparanase. J. Surg. Res. 67:98–105.

50 Kovalszky, I., Z. Scharff, and A. Jeney. 1993. Potential markers (enzymes, proteoglycans) for human liver tumors. Acta Biomed. Ateneo Parmense 64:157–163.

51 Kramer, E. L., Liebes, L., Wasserheit, C., Noz, M. E., Blank, E. W., Zabalegui, A., Melamed, J., Furmanski, P., Peterson, J. A. Initial Clinical valuation of adiolabeled 51. MX-DTPA humanized BrE-3 antibody in patients with adavanced breast cancer. Clin.Cancer RES.,4. 1679–1688, 1998.

52. Kumar R, Fidler I J. Angiogenic molecules and cancer metastasis. In Vivo 1998; 12:27–34.

53. Lambrecht, V., Bourhis, X. L., Toillon, R., Boilly, B., and Hondermarck, H. Alterations in both heparan sulfate proteoglycans and mitogenic activity of fibroblast growth factor-2 triggered by inhibitors of proliferation in normal and breast cancer epitherial cells. Exp.Cell.Res., 245: 239–244, 1998.

54. Lander, A. D. Targeting the glycosaminoglycan-binding sites on proteins. Chem.Biol., 1: 73–78, 1994.

55. Lander, A. D., C. S. Stipp, and J. K. Ivins. 1995. The glypican family of heparan sulfate proteoglycans: major cell-surface proteoglycans of the developing nervous system. Perspect. Dev. Neurobiol. 1:1–7.

56. Lange, C. A., Richer, J. K., Shen, T., and Horwitz, K. B. Convergence of progesterone and epidermal growth factor signaling in breast cancer. J.Biol. Chem., 273: 31308–31316, 1998.

57. LaRochelle, W. J., Sakaguchi, K., Atabey, N., Cheon, H., Takagi, Y., Kinaia, T., Day, R. M., Miki, T., Burgess, W. H., and Bottaro, D. P. Heparan sulfate proteoglycan modulates keratinocyte growth factor signaling through interaction with both ligand and receptor. Biochemistry, 38: 1765–1771, 1999.

58. Laskov, R., R. I. Michaeli, H. Sharir, E. Yefenof, and I. Vlodavsky. 1991. Production of heparanase by normal and neoplastic murine B-lymphocytes. Int. J. Cancer. 47:92–98.

59. LeBaron, R. G., A. Höök, J. D. Esko, S. Gay, and M. Höök. 1989. Binding of heparan sulfate to type V collagen. A mechanism of cell-substrate adhesion. J. Biol. Chem. 264:7590–7956.

60. Levine, A. J. p53, the cellular gatekeeper for growth and division. Cell, 88: 323–331, 1997.

61. Levy, P., A. Munier, S. Baron-Delage, Y. DiGioia, C. Gespach, J. Capeau, and G. Cherqui. 1996. Syndecan-1 alterations during the tumorigenic progress of human colonic Caco-2 cells induced by human Ha-ras or polyoma middle T oncogenes. Br. J.Cancer 74:423–421.

62. Lindsay, S., M. Ireland, O. O'Brien, J. Clayton-Smith, J. A. Hurst, J. Mann, T. Cole, J. Sampson, S. Slaney, D. Schlesinger, J. Burn, and G. Pilia. 1997. Large scale deletions of the GPC3 gene may account for a minority of cases of Simpson-Golabi-Behmel syndrome. J. Med. Genet. 34:480–483.

63. Litwack, E. D., C. S. Stipp, A. Kumbasar, and A. D. Lander. 1994. Neuronal expression of glypican, a cell-surface glycosylphosphatidylinositol-anchored heparan sulfate proteoglycan, in the adult rat nervous system. J. Neuroscience. 14:3713–3724.

64. Litwack, E. D., J. K. Ivins, A. Kumbasar, S. Paine-Saunders, C. S. Stipp, and A. D. Lander. 1998. Expression of the heparan sulfate proteoglycan glypican-1 in the developing rodent. Dev. Dynamics. 211:72–87.

65. Liu W, Litwack E D, Stanley M J, Langford J K, Lander A D, Sanderson R D. Heparan sulfate proteoglycans as adhesive and anti-invasive molecules. Syndecans and glypican have distinct functions. J Biol Chem Aug. 28, 1998;273(35):22825–32.

66. Lizard-Nacol, S., Lidereau, R., Collin, F., Arnal, M., Hahnel, L., Roignot, P., Cruisenier, J., and Guerrin, J. Benign breast disease: absence of genetic alterations at several loci implicated in breast cancer malignancy. Cancer Res., 55: 4416–4419, 1995.

67. Miyaza, Y., Y. Shinomura, S. Higashiyma, S. Kanayama, Y. Higashimoto, S. Tsutsui, S. Zushi, N. Taniguchi, and Y. Matsuzawa. 1996. Heparin-binding EGF-like growth factor is an autocrine growth factor for rat gastric epithelial cells. Biochem. Biophys. Res. Commun. 223: 36–41.

68. Nackaerts, K., E. Verbeken, G. Deneffe, B. Vandershueren, M. Demedts, and G. David. 1997. Heparan sulfate proteoglycan expression in human lung-cancer cells. Int. J. Cancer 74:335–345.

69. Nakato, H., T. A. Futch, and S. B. Selleck. 1995. The division abnormally delayed (dally) gene: a putative integral membrane proteoglycan required for cell division patterning during postembryonic development of the nervous system in Drosophila. Development. 121:3687–3702.

70. Nass, S. J., and Dickson, R. B. Defining a role for c-Myc in breast tumorigenesis. Breast Cancer Res. Treat., 44: 1–22, 1997.

71. Olayioye, M. A., Beuvink, I., Horsch, K., Daly, J. M., and Hynes, N. E. ErbB receptor-induced activation of Stat transcription factors is mediated by Src tyrosine kinase. J.Biol.Chem., 274: 17209–17218, 1999.

72. Olwin, B. B. and A. Rapraeger. 1992. Repression of myogenic differentiation by aFGF, bFGF, and K-FGF is dependent on cellular heparan sulfate. J. Cell Biol. 118: 631–639.

73. Ornitz, D. M., A. Yayon, J. G. Flanagan, C. M. Svahn, E. Levi, and P. Leder. 1992. Heparin is required for cell-free binding of basic fibroblast growth factor to a soluble receptor and for mitogenesis in whole cells. Mol. Cell. Biol. 12:240–247.

74. Paine-Saunders, S., Viviano, B. L., and Saunders, S. GPC6, a novel member of the glypican gene family, encodes a product structurally related to GPC4 and is colocalized with GPC5 on human chromosome 13. Genomics, 57: 455–458, 1999.

75. Pantoliano, M. W., R. A. Horlick, B. A. Springer, D. E. Van Dick, T. Tobery, D. R. Wetmore, J. D. Lear, A. T. Nahapetian, J. D. Bradley, and W. O. Sisk. 1994. Multivalent ligand-receptor binding interactions in the fibroblast growth factor system produce a cooperative growth factor and heparin mechanism for receptor dimerization. Biochemistry. 33:10229–10248.

76. Pegram, M., Hsu, S., Lewis, G., Pietras, R., Beryt, M., Sliwkowski, M., Coombs, D., Baly, D., Kabbinavar, F., and Slamon, D. J. Inhibitory effects of combinations of HER2/neu antibody and chemotherapeutic agents used for treatment of human breast cancers. Oncogene., 18: 2241–2251, 1999.

77. Pegram, M. D., Lipton, A., Hayes, D. F., Weber, B. L., Baselga, J. M., Tripathy, D., Baly, D., Baughman, S. A., Twaddell, T., Glaspy, J. A., and Slamon, D. J. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. J.Clin.Oncol., 16: 2659–2671, 1998.

78. Penc, S. F., Pomahac, B., Winkler, T., Dorschner, R. A., Eriksson, E., Herndon, M., and Gallo, R. L. Dermatan sulfate released after injury is a potent promoter of fibroblast growth factor-2 function. J.Biol.chem., 273: 28116–28121, 1998.

79. Pilia, G., R. M. Hughes-Benzie, A. MacKenzie, P. Baybayan, E. Y. Chen, R. Huber, G. Neri, A. Cao, A. Forabosco, and D. Schlessinger. 1996. Mutations in GPC3, a glypican gene, cause the Simpson-Golabi-Behmel overgrowth syndrome. Nat. Genet. 12:124–247.

80 Ponzone, R., and Baum, M. The BRCA paradox in breast and ovarian cancer. Eur.J.Cancer, 34: 966–967, 1998.

81 Prigent, S. A. and N. R. Lemoine. 1992. The type 1 (EGFR-related) family of growth factor receptors and their ligands. Prog. Growth Factor Res. 4:1–24.

82 Quenel, N., Wafflart, J., Bonichon, F., de Mascarel, I., Trojani, M., Durand, M., Avril, A., and Coindre, J. M. The prognostic value of c-erbB2 in primary breast carcinomas: a study on 942 cases. Breast Cancer Res. Treat., 35: 283–291, 1995.

83 Raab, G. and M. Klagsbrun. 1997. Heparin-binding EGF-like growth factor. Biochem. Biophys. Acta. 1333: F179–199, 1997.

84 Rahmoune, H., Chen, H., Gallagher, J. T., Rudland, P. S., and Fernig, D. G. Interaction of heparan sulfate from mammary cells with acidic fibroblast growth factor (FGF) and basic FGF. J.Biol. Chem., 273: 7303–7310, 1998.

85 Rahmoune, H., Rudland, P. S., Gallagher, J. T., and Fernig, D. G. Hepatocyte growth factor/scatter factor has distinct classes of binding site in heparan sulfate from mammary cells. Biochemistry, 37: 6003–6008, 1998.

86 Raitano, A. B. and M. Korc. 1990. Tumor necrosis factor up-regulates γ-interferon binding in a human carcinoma cell line. J. Biol. Chem. 265:10466–10472.

87 Rapraeger, A. C., A. Krufka, and B. B. Olwin. 1991. Requirement of heparan sulfate for bFGF-mediated fibroblast growth and myoblast differentiation. Science. 252: 1705–1708.

88 Rapraeger, A. C., M. Jalkanen, E. Endo, J. Koda, and M. Bernfield. 1995. The cell surface proteoglycan from mouse mammary epithelial cells bears chondroitin sulfate and heparan sulfate glycosaminoglycans. J. Biol. Chem. 260:11046–11052.

89 Rapraeger, A. C., S. Guimond, A. Krufka, and B. B. Olwin. 1994. Regulation by heparan sulfate in fibroblast growth factor signaling. Methods Enzymol. 245:219–40.

90 Reichsman, F., L. Smith, and S. Cumberledge. 1996. Glycosaminoglycans can modulate extracellular localization of the wingless protein and promote signal transduction. J. Cell Biol. 135:819–27.

91 Rodrigues, M. L., Presta, L. G., Kotts, C. E., Wirth, C., Mordenti, J., Osaka, G. Wong, W. L. T., Nuijens, A., Blackburn, B., and Carter, P. Development of a humanized disulfide-stabilized anti-p185HER2 Fv—lactamase fusion protein for activation of a cephalosporin doxorubicin prodrug. Cancer Res., 55: 63–70, 1995.

92 Roghani, M., A. Mansukhani, P. Dell'Era, P. Bellosta, C. Basilico, and D. Moscatelli. 1994. Heparin increases the affinity of basic fibroblast growth factor for its receptor but is not required for binding. J. Biol. Chem. 269:3976–3984.

93 Rudland, P. S., Barraclough, R., Fernig, D. G., and Smith, J. A. Mammary stem cells in normal development and cancer. In "Stem Cells and Cancer" (C.Potton,Ed.), Churchill Livingstone., 1997.

94 Sakata, H., S. J. Stahl, W. G. Taylor, J. M. Rosenberg, K. Sakaguchi, P. T. Wingfield, and J. S. Rubin. 1997. Heparin binding and oligomerization of hepatocyte growth factor/scatter factor isoforms. Heparan sulfate glycosaminoglycan requirement for Met binding and signaling. J. Biol. Chem. 272:9457–63.

95 Saksela, O. and D. B. Rifkin. 1990. Release of basic fibroblast growth factor-heparan sulfate complexes from endothelial cells by plasminogen activator-mediated proteolytic activity. J. Cell Biol. 110:767–775.

96 Saksela, O., Moscatelli, D., Sommer, A., and Rifkin, D. B. Endothelial cell-derived heparan sulfate binds basic fibroblast growth factor and protects it from proteolytic degradation. J.Cell Biol., 107: 743–751, 1988.

97 Saunders, S., S. Paine-Saunders, and A. D. Lander. 1997. Expression of the cell surface glypican-5 is developmentally regulated in kidney, limb, and brain. Dev. Biol. 190:78–93.

98 Schaefer, G., Akita, R. W., and Sliwkowski, M. X. A discrete three-amino acid segment (LVI) at the C-terminal end of kinase-impared ErbB3 is required for transactivation of ErbB2. J.Biol.Chem., 274: 859–866, 1999.

99 Schlessinger, J., I. Lax, and M. Lemmon. 1995. Regulation of growth factor activation by proteoglycans: what is the role of the low affinity receptors? Cell. 83:357–360.

100 Schwarz, L. C., T. Inoue, T. Irimura, J. E. Damen, A. H. Greenberg, and J. A. Wright. 1990. Relationships between heparanase activity and increasing metastatic potential of fibroblasts transfected with various oncogenes. Cancer Lett. 51:187–192.

101 Slamon, D. J., Leyland-Jones, B., Shak, S., Fuchs, H., Paton, V., Bajamonde, A., Fleming, T., Eiermann, W., Wolter, J., Pegram, M., Baselga, J., and Norton, L. Use of chemotherapy plus a monoclonal antibody against HER2 for metastatic breast cancer that overexpresses HER2. N. Engl. J. Med., 344: 783–792, 2001.

102 Sommer, A., and Rifkin, D. B. Interaction of heparin with human basic fibroblast growth factor: Protection of the angiogenic protein from proteolytic degradation bye a glycosaminoglycan. J.Cell Physiol., 138: 215–220, 1989.

103 Spivak-Kroizman, T., M. A. Lemmon, I. Dikic, J. E. Landbury, D. Pinchasi, J. Huang, M. Jaye, C. Crumley, J. Schlessinger, and I. Lax. 1994. Heparin-induced oliogomerization of FGF molecules is responsible for FGF receptor dimerization, activation, and cell proliferation. Cell. 79:1015–1024.

104 Stanley, M. J., B. F. Liebersbach, W. Liu, D. J. Anhalt, and R. D. Sanderson. 1995. Heparan sulfate mediated cell aggregation syndecans-1 and -4 mediate intercellular adhesion following their transfection into human B-lymphoid cells. J. Biol. Chem. 10:5077–5083.

105 Stanley, M. J., Stanley, M. W., Sanderson, R. D., and Zera, R. Syndecan-1 expression is induced in the stroma of infiltrating breast carcinoma. Am. J. Clin. Pathol., 112: 377–383, 1999.

106 Steinfeld, R., Berghe, H. V. D., and David, G. Stimulation of fibroblast growth factor receptor-1 occupancy and signaling by cell surface-associated syndecans and glypican. J.Cell Biol., 133: 405–416, 1996.

107 Stipp, C. S., E. D. Litwack, and A. D. Lander. 1994. Cerebroglycan: an integral membrane heparan sulfate proteoglycan that is unique to the developing nervous system and expressed specifically during neuronal differentiation. J. Cell. Biol. 124:149–160.

108 Stipp, C. S., Litwack, E. D., and Lander, A. D. Cerebroglycan: an integral membrane heparan sulfate proteoglycan that is unique to the developing nervous system and expressed specifically during neuronal differentiation. J.Cell Biol., 111: 3165–3176, 1994.

109 Stipp, C. S., Litwack, E. D., and Lander, A. D. Cerebroglycan: an integral membrane heparan sulfate proteoglycan that is unique to the developing nervous system and expressed specifically during neuronal differentiation. J. Cell Biol., 111: 3165–3176, 1994.

110 Veugelers, M., Cat B. D., Ceulemans H., Bruystens, A. M., Coomans, C., Dürr, J., Vermeesch, J., Marynen, P., and David, G. Glypican-6, a new member of the glypican 111 Vlodavsky, I., H. -Q. Miao, B. Medalion, P. Danagher, and D. Ron. 1996. Involvement of heparan sulfate and related molecules in sequestration and growth promoting activity of fibroblast growth factor. Cancer Metastasis Rev. 15:177–186.

112 Wagner M, Cao T, Lopez M E, Hope C, van Nostrand K, Kobrin M S, Fan H U, Bëchler, M W, Korc M. Expression of a truncated EGF receptor is associated with inhibition of pancreatic cancer cell growth and enhanced sensitivity to cisplatinum. Int J Cancer 1996; 68:782–787.

113 Wagner M, Lopez M E, Cahn M, Korc M. Suppression of fibroblast growth factor receptor signaling inhibits pancreatic cancer growth in vitro and in vivo. Gastroenterology 1998; 114:798–807.

114 Walker, R. A. The erbB/HER type 1 tyrosine kinase receptor family. J. Pathol., 185: 234–235, 1998.

115 Wang, Z., Zhang, L., Yeung, T. K., and Chen, X. Endocytosis deficiency of epidermal growth factor (EGF) receptor-ErbB2 heterodimers in response to EGF stimulation. Mol.Biol.Cell, 10: 1621–1636, 1999.

116 Warshaw, A. L. and C. Fernandez-del Castillo. 1992. Pancreatic carcinoma. N. Engl. J. Med. 326:455–465.

117 Watanabe, K., H. Yamada, and Y. Yamaguchi. 1995. K-glypican: a novel GPI-anchored heparan sulfate proteoglycan that is highly expressed in developing brain and kidney. J. Cell Biol. 130:1207–18.

118 Wong, L., Deb, T. B., Thompson, S. A., Wells, A., and Johnson, G. R. A differential requirement for the COOH-terminal region of the epidermal growth factor (EGF) receptor in amphiregulin and EGF mitogenic signaling. J.Biol.Chem., 274: 8900–8909, 1999.

119 Yamanaka, Y., H. Friess, M. Büchler, H. G. Beger, E. Uchida, M. Onda, M. S. Kobrin, and M. Korc. 1993. Overexpression of acidic and basic fibroblast growth factors in human pancreatic cancer correlates with advanced tumor stage. Cancer Res. 53:5289–5296.

120 Yayon, A., M. Klagsbrun, J. D. Esko, P. Leder, and D. M. Ornitz. 1991. Cell surface, heparin-like molecules are required for binding of basic fibroblast growth factor to its high affinity receptor. Cell. 64:841–848.

What is claimed is:

1. A method for diagnosing human breast cancer comprising the steps of contacting a molecule selected from the group consisting of an antibody and an antibody fragment that binds to glypican-1 with either a body fluid or body tissue, and detecting the molecule bound to glypican-1.

2. The method of claim 1, wherein the molecule comprises an antibody.

3. The method of claim 2, wherein the antibody detects breast cancer from the presence of glypican-1 in body fluid.

4. The method of claim 2, wherein the antibody detects breast cancer from the presence of glypican-1 in body tissue.

* * * * *

UNITED STATES PATENT AND TRADEMARK OFFICE
CERTIFICATE OF CORRECTION

| | | |
|---|---|---|
| PATENT NO. | : 7,108,986 B2 | Page 1 of 1 |
| APPLICATION NO. | : 10/210327 | |
| DATED | : September 19, 2006 | |
| INVENTOR(S) | : Murray Korc et al. | |

It is certified that error appears in the above-identified patent and that said Letters Patent is hereby corrected as shown below:

Column 1, line 16 please insert the following:

--This invention was made with Government support under Grant Nos. CA40562 & NS26862 awarded by the National Institutes of Health. The Government has certain rights in this invention--

Signed and Sealed this

Nineteenth Day of December, 2006

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 29
<212> TYPE: DNA
<213> ORGANISM: Artificial
<220> FEATURE:
<223> OTHER INFORMATION: sense primer for Glypican 3 with EcoRI and
      BamHI site

<400> SEQUENCE: 1
agtggatccc tgctcttact gccagggac                                        29

<210> SEQ ID NO 2
<211> LENGTH: 29
<212> TYPE: DNA
<213> ORGANISM: Artificial
<220> FEATURE:
<223> OTHER INFORMATION: antisense Glypican-3 primer with EcoRI and
      BamHI site

<400> SEQUENCE: 2
gtagaattcg ctttcctgca ttcttctgg                                        29

<210> SEQ ID NO 3
<211> LENGTH: 29
<212> TYPE: DNA
<213> ORGANISM: Artificial
<220> FEATURE:
<223> OTHER INFORMATION: sense Glypican-4 primer with EcoRI and BamHI
      site.

<400> SEQUENCE: 3
agtggatccg ttgacaccag caaaccaga                                        29

<210> SEQ ID NO 4
<211> LENGTH: 29
<212> TYPE: DNA
<213> ORGANISM: Artificial
<220> FEATURE:
<223> OTHER INFORMATION: antisense Glypican-4 primer with EcoRI and
```

BamHI site

<400> SEQUENCE: 4
gtagaattca gtgaggaggt aggcctgtg          29

<210> SEQ ID NO 5
<211> LENGTH: 25
<212> TYPE: DNA
<213> ORGANISM: Artificial
<220> FEATURE:
<223> OTHER INFORMATION: sense primer for VSVGTMR with EcoRI and XbaI
      site

<400> SEQUENCE: 5
gccacgtgtc cattgcctct ttttc             25

<210> SEQ ID NO 6
<211> LENGTH: 26
<212> TYPE: DNA
<213> ORGANISM: Artificial
<220> FEATURE:
<223> OTHER INFORMATION: antisense primer for VSVMTR with EcoRI and XbaI
      site

<400> SEQUENCE: 6
gctctagact aaagcttgag aaccaa            26

<210> SEQ ID NO 7
<211> LENGTH: 49
<212> TYPE: PRT
<213> ORGANISM: Artificial
<220> FEATURE:
<223> OTHER INFORMATION: transmembrane domain of vesicular stomatitis
      virus from glypican-1 VSVGMTR construct.

<400> SEQUENCE: 7

```
His Val Ser Ile Ala Ser Phe Phe Phe Ile Ile Gly Leu Ile Ile Gly
1               5                   10                  15

Leu Phe Val Val Leu Lys Leu Ser Arg Gly Pro Phe Glu Gln Lys Leu
            20                  25                  30

Ile Ser Glu Glu Asp Leu Asn Met His Thr Gly His His His His His
        35                  40                  45

His
```

<210> SEQ ID NO 8
<211> LENGTH: 29
<212> TYPE: DNA
<213> ORGANISM: Artificial
<220> FEATURE:
<223> OTHER INFORMATION: sense primer for Glypican-1 containing ECORI and HindIII sites

<400> SEQUENCE: 8
gtagaattcg gaccttggct ctgcccttc 29

<210> SEQ ID NO 9
<211> LENGTH: 29
<212> TYPE: DNA
<213> ORGANISM: Artificial
<220> FEATURE:

```
<223> OTHER INFORMATION: antisense primer for Glypican-1 containing
      ECORI and HindIII sites

<400> SEQUENCE: 9
agtaagcttg taagggccag gaagaggag                                          29
```